US010876144B2

(12) United States Patent
Centanni et al.

(10) Patent No.: US 10,876,144 B2
(45) Date of Patent: *Dec. 29, 2020

(54) PROCESS FOR DETERMINING VIABILITY OF TEST MICROORGANISMS OF BIOLOGICAL INDICATOR AND STERILIZATION DETECTION DEVICE FOR DETERMINING SAME

(71) Applicant: American Sterilizer Company, Mentor, OH (US)

(72) Inventors: Michael A. Centanni, Parma, OH (US); Phillip P. Franciskovich, Concord, OH (US)

(73) Assignee: American Sterilizer Company, Mentor, OH (US)

( * ) Notice: Subject to any disclaimer, the term of this patent is extended or adjusted under 35 U.S.C. 154(b) by 193 days.

This patent is subject to a terminal disclaimer.

(21) Appl. No.: 15/699,191

(22) Filed: Sep. 8, 2017

(65) Prior Publication Data

US 2019/0017091 A1     Jan. 17, 2019

Related U.S. Application Data

(60) Provisional application No. 62/532,512, filed on Jul. 14, 2017.

(51) Int. Cl.
*C12Q 1/22* (2006.01)
*A61L 2/28* (2006.01)
(Continued)

(52) U.S. Cl.
CPC ............. *C12Q 1/22* (2013.01); *A61L 2/28* (2013.01); *C12M 37/06* (2013.01); *G01N 2033/4977* (2013.01)

(58) Field of Classification Search
None
See application file for complete search history.

(56) References Cited

U.S. PATENT DOCUMENTS 3,164,004 A   1/1965   King, Jr.
3,327,519 A   6/1967   Crawford
(Continued)

FOREIGN PATENT DOCUMENTS

EP    0821228    1/1998
EP    0930368    7/1999
(Continued)

OTHER PUBLICATIONS

Fairchild, Tim M; Foegeding, PM; "A Proposed Nonpathogenic Biological Indicator for Thermal Inactivation of Listeria monocytogenes" Applied and Environmental Microbiology, 59, 1247-1250, 1993 (Year: 1993).*

(Continued)

*Primary Examiner* — David W Berke-Schlessel
(74) *Attorney, Agent, or Firm* — Renner, Otto, Boisselle & Sklar, LLP

(57) ABSTRACT

A process for determining the viability of a biological indicator includes exposing the biological indicator to a viability detection medium, the biological indicator including test microorganisms, the exposing the biological indicator to the viability detection medium producing a gaseous reaction product when one or more of the test microorganisms are viable. The presence or absence of the gaseous reaction product produced by the biological indicator combined with the viability detection medium is detected with a sensing device, the sensing device comprising an electromechanical sensor, wherein the presence of the gaseous reaction product indicates the presence of viable test microorganisms and the absence of the gaseous reaction product indicates the absence of viable test microorganisms. A (Continued)

sterilization detection device includes a container configured to contain the biological indicator, a viability detection medium, and the sensing device.

25 Claims, 8 Drawing Sheets

(51) Int. Cl.
G01N 33/497 (2006.01)
C12M 1/12 (2006.01)

(56) References Cited

U.S. PATENT DOCUMENTS

| | | |
|---|---|---|
| 3,464,797 A | 9/1969 | Hagopain |
| 4,073,691 A | 2/1978 | Ahnell et al. |
| 4,111,036 A | 9/1978 | Frechette et al. |
| 4,123,700 A | 10/1978 | LaConti et al. |
| 4,163,384 A | 8/1979 | Blakemore |
| 4,171,253 A | 10/1979 | Nolan et al. |
| 4,236,893 A | 12/1980 | Rice |
| 4,242,096 A | 12/1980 | Oliveria et al. |
| 4,314,821 A | 2/1982 | Rice |
| 4,444,892 A | 4/1984 | Malmros |
| 4,522,690 A | 6/1985 | Venkatasetty |
| 4,563,893 A | 1/1986 | Tanyolac et al. |
| 4,664,757 A | 5/1987 | Zupancic et al. |
| 4,788,466 A | 11/1988 | Paul et al. |
| 4,822,566 A | 4/1989 | Newman |
| 4,849,178 A | 7/1989 | Azuma |
| 4,865,717 A | 9/1989 | Setter et al. |
| 4,908,188 A | 3/1990 | Jeffries et al. |
| 4,910,149 A | 3/1990 | Okube et al. |
| 4,925,544 A | 5/1990 | Goldring |
| 4,948,496 A | 8/1990 | Chand |
| 5,145,645 A | 9/1992 | Zakin et al. |
| 5,202,261 A | 4/1993 | Musho et al. |
| 5,250,439 A | 10/1993 | Musho et al. |
| 5,286,448 A | 2/1994 | Childers |
| 5,302,274 A | 4/1994 | Tomantschger et al. |
| 5,310,507 A | 5/1994 | Zakin et al. |
| 5,312,762 A | 5/1994 | Guiseppi-Elie |
| 5,322,611 A | 6/1994 | Zaromb |
| 5,338,412 A | 8/1994 | Burk et al. |
| 5,339,675 A | 8/1994 | DiLeo et al. |
| 5,352,574 A | 10/1994 | Guiseppi-Elie |
| 5,372,785 A | 12/1994 | Johnson et al. |
| 5,389,336 A | 2/1995 | Childers |
| 5,445,792 A | 8/1995 | Rickloff et al. |
| 5,518,895 A | 5/1996 | Thorpe et al. |
| 5,527,446 A | 6/1996 | Kosek et al. |
| 5,527,508 A | 6/1996 | Childers et al. |
| 5,595,908 A | 1/1997 | Fawcett et al. |
| 5,608,156 A | 2/1997 | Ando et al. |
| 5,651,922 A | 7/1997 | Nahass et al. |
| 5,683,570 A | 11/1997 | Pacey et al. |
| 5,700,375 A | 12/1997 | Hagen et al. |
| 5,705,399 A | 1/1998 | Larue |
| 5,736,355 A | 4/1998 | Dyke et al. |
| 5,756,631 A | 5/1998 | Grate |
| 5,756,879 A | 5/1998 | Yamagishi et al. |
| 5,766,787 A | 6/1998 | Watanabe et al. |
| 5,766,934 A | 6/1998 | Guiseppi-Elie |
| 5,807,701 A | 9/1998 | Payne et al. |
| 5,849,174 A | 12/1998 | Sanghera et al. |
| 5,856,198 A | 1/1999 | Joffe et al. |
| 5,866,798 A | 2/1999 | Schonfeld et al. |
| 5,882,590 A | 2/1999 | Stewart et al. |
| 5,958,214 A | 9/1999 | Nikolskaja |
| 5,958,787 A | 9/1999 | Schonfeld et al. |
| 6,077,480 A | 6/2000 | Edwards et al. |
| 6,171,867 B1 | 1/2001 | Feucht et al. |
| 6,189,368 B1 | 2/2001 | Ichida et al. |
| 6,196,052 B1 | 3/2001 | May et al. |
| 6,241,873 B1 | 6/2001 | Namba et al. |
| 6,303,096 B1 | 10/2001 | Yamamoto et al. |
| 6,410,332 B1 | 6/2002 | Desrosiers et al. |
| 6,517,775 B1 | 2/2003 | Wang et al. |
| 6,537,491 B1 | 3/2003 | Wang et al. |
| 6,558,529 B1 | 5/2003 | McVey et al. |
| 6,560,551 B1 | 5/2003 | Severson et al. |
| 6,581,435 B2 | 6/2003 | Wang et al. |
| 6,630,560 B2 | 10/2003 | McGill et al. |
| 6,631,333 B1 | 10/2003 | Lewis et al. |
| 6,844,742 B2 | 1/2005 | Centanni |
| 6,897,661 B2 | 5/2005 | Allen et al. |
| 6,909,972 B2 | 6/2005 | Centanni |
| 6,917,885 B2 | 7/2005 | Centanni |
| 6,927,582 B2 | 8/2005 | Kaiser et al. |
| 6,930,493 B2 | 8/2005 | Kaiser et al. |
| 6,933,733 B2 | 8/2005 | Korenev et al. |
| 6,946,852 B2 | 9/2005 | Centanni |
| 6,960,921 B2 | 11/2005 | Kaiser et al. |
| 6,992,494 B2 | 1/2006 | Kaiser |
| 7,232,545 B2 | 6/2007 | Centanni et al. |
| 7,431,886 B2 | 10/2008 | Centanni |
| 7,527,766 B2 | 5/2009 | Centanni |
| 7,541,002 B2 | 6/2009 | Centanni |
| 7,611,667 B2 | 11/2009 | Centanni |
| 7,828,956 B2 | 11/2010 | Ding et al. |
| 7,901,618 B2 | 3/2011 | Centanni |
| 7,918,977 B2 | 4/2011 | Dorisio Deininger et al. |
| 7,955,560 B2 | 6/2011 | Centanni |
| 8,171,795 B1 | 5/2012 | Mutharasan et al. |
| 8,372,624 B2 | 2/2013 | Franciskovich et al. |
| 8,507,248 B2 | 8/2013 | Franciskovich et al. |
| 8,679,806 B2 | 3/2014 | Levon et al. |
| 8,815,574 B2 | 8/2014 | Bachur, Jr. et al. |
| 8,945,837 B2 | 2/2015 | Franciskovich et al. |
| 9,362,980 B2 | 6/2016 | Han et al. |
| 9,400,272 B2 | 7/2016 | Bachur, Jr. et al. |
| 2001/0039033 A1 | 11/2001 | Ogawa |
| 2002/0014410 A1 | 2/2002 | Silveri et al. |
| 2003/0086820 A1 | 5/2003 | McDonnell |
| 2003/0132279 A1 | 7/2003 | Stemmie |
| 2004/0026246 A1 | 2/2004 | Chapples et al. |
| 2004/0092004 A1 | 5/2004 | Stanford, Jr. et al. |
| 2004/0129562 A1 | 7/2004 | Shuk et al. |
| 2004/0262170 A1 | 12/2004 | Centanni |
| 2005/0063882 A1 | 3/2005 | Centanni et al. |
| 2005/0170255 A1 | 8/2005 | Koh et al. |
| 2005/0244696 A1 | 11/2005 | Kuromatsu et al. |
| 2006/0096871 A1 | 5/2006 | Manoukian et al. |
| 2006/0254908 A1 | 11/2006 | Grant et al. |
| 2007/0003995 A1 | 1/2007 | Song et al. |
| 2007/0102294 A1 | 5/2007 | Dorisio Deininger et al. |
| 2007/0144236 A1 | 6/2007 | Stokes et al. |
| 2008/0047847 A1 | 2/2008 | Schmidt et al. |
| 2008/0070231 A1 | 3/2008 | Franciskovich et al. |
| 2008/0070272 A1 | 3/2008 | Franciskovich et al. |
| 2009/0047176 A1 | 2/2009 | Cregger |
| 2009/0084159 A1 | 4/2009 | Sun et al. |
| 2009/0101501 A1 | 4/2009 | Tao et al. |
| 2009/0117603 A1 | 5/2009 | Franciskovich et al. |
| 2009/0212782 A1 | 8/2009 | Silveri |
| 2009/0317724 A1 | 12/2009 | Kumar et al. |
| 2010/0248296 A1 | 9/2010 | Franciskovich et al. |
| 2010/0267044 A1 | 10/2010 | Franciskovich et al. |
| 2010/0304215 A1 | 12/2010 | Suh et al. |
| 2011/0076192 A1 | 3/2011 | Robitaille et al. |
| 2011/0086368 A1 | 4/2011 | Shih et al. |
| 2012/0021406 A1 | 1/2012 | Franciskovich et al. |
| 2012/0196355 A1 | 8/2012 | Franciskovich et al. |
| 2012/0214154 A1 | 8/2012 | Franciskovich et al. |
| 2012/0258444 A1 | 10/2012 | Therrien et al. |
| 2012/0293189 A1 | 11/2012 | Qureshi et al. |
| 2013/0089922 A1 | 4/2013 | Franciskovich et al. |
| 2013/0199955 A1 | 8/2013 | Franciskovich et al. |
| 2013/0217001 A1 | 8/2013 | Franciskovich et al. |
| 2013/0217107 A1 | 8/2013 | Pederson et al. |
| 2013/0224849 A1 | 8/2013 | Chandrapati et al. |
| 2013/0273594 A1 | 10/2013 | Ahimon et al. |
| 2014/0162307 A1 | 6/2014 | Franciskovich et al. |
| 2014/0262829 A1 | 9/2014 | Franciskovich et al. |

(56) References Cited

U.S. PATENT DOCUMENTS

| | | |
|---|---|---|
| 2014/0273054 A1 | 9/2014 | Franciskovich et al. |
| 2014/0273072 A1 | 9/2014 | Franciskovich et al. |
| 2014/0273073 A1 | 9/2014 | Franciskovich et al. |
| 2015/0042364 A1 | 2/2015 | Bachur, Jr. et al. |
| 2015/0147773 A1 | 5/2015 | Franciskovich et al. |
| 2015/0233852 A1 | 8/2015 | Bommarito et al. |
| 2015/0337354 A1 | 11/2015 | Ahimou et al. |

FOREIGN PATENT DOCUMENTS

| | | |
|---|---|---|
| EP | 1542299 | 6/2005 |
| EP | 2136431 | 12/2009 |
| EP | 3168608 | 5/2017 |
| JP | 60-130398 | 7/1985 |
| JP | 06160343 | 6/1994 |
| JP | 8201336 | 8/1996 |
| JP | 2000097906 | 4/2000 |
| JP | 2003344347 | 12/2003 |
| JP | 2009500609 | 1/2009 |
| WO | WO 95/33848 | 12/1995 |
| WO | WO 02/14490 | 2/2002 |
| WO | WO 2008/079469 | 7/2008 |
| WO | WO 2008/118564 A1 | 10/2008 |
| WO | WO 2009/005252 | 1/2009 |

OTHER PUBLICATIONS

Supplemental Written Opinion for related International Application No. PCT/US2018/041584 dated Jun. 17, 2019.

Supplemental Written Opinion for related International Application No. PCT/US2018/041589 dated Jun. 17, 2019.

Supplemental Written Opinion for related International Application No. PCT/US2018/041594 dated Jun. 17, 2019.

Fengjiao He et al; "A Novel QCM-based Biosensor for Detection of Microorganisms Producing Hydrogen Sulfide", Analytical Letters, vol. 41, No. 14, Oct. 31, 2008, pp. 2697-2709.

Ren et al; "A new B-PAn-P system for the detection of bacteria population", Sensors and Actuators B: Chemical: International Journal Devoted to Research and Development of Physical and Chemical Transducers, Elsevier BV, NL, vol. 125, No. 2, Jul. 27, 2007, pp. 510-516.

Sandeep Kumar Vashist et al; "Recent Advances in Quartz Crystal Microbalance-Based Sensors", Journal of Sensors, vol. 2011, Jan. 1, 2011, pp. 1-13.

John G. Webster et al; "Resistive Gas Sensors" In: "Wiley Encyclopedia of Electrical and Electronics Engineering", Nov. 16, 2016, John Wiley & Sons, Inc., Hoboken, pp. 1-12.

Ileana Andreea Ratiu et al; "Discrimination of bacteria by rapid sensing their metabolic volatiles using an aspiration-type ion mobility spectrometer (a-IMS) and gas chromatography-mass spectrometry GC-MS", Analytica Chimica Acta, vol. 982, Jun. 22, 2017, pp. 209-217.

Jan Oberlaender et al; "Study of Interdigitated Electrode Arrays Using Experiments and Finite Element Models for the Evaluation of Sterilization Processes", Sensors, vol. 15. No. 10. Oct. 14, 2015, pp. 26115-26127.

Edin Terzic et al; "Capacitive Sensing Technology" In: "A Neural Network Approach to Fluid Quantity Measurement in Dynamic Environments", Jan. 1, 2012, Springer London, London, XP055391341, ISBN: 978-1-4471-4060-3 pp. 11-37.

Xiao Liu et al; "A Survey on Gas Sensing Technology", Sensors, Jul. 1, 2012, pp. 9635-9665.

International Search Report for related International Application No. PCT/US2018/041584 dated Sep. 24, 2018.

International Search Report for related International Application No. PCT/US2018/041589 dated Sep. 24, 2018.

International Search Report for related International Application No. PCT/US2018/041594 dated Sep. 24, 2018.

U.S. Appl. No. 15/699,220, filed Sep. 8, 2017, and pending claims.

U.S. Appl. No. 15/699,240, filed Sep. 8, 2017, and pending claims.

Albert et al.; "Biological indicators for steam sterilization: characterization of a rapid biological indicator utilizing Bacillus stearothermophilus spore-associated alpha-glucosidase enzyme"; Journal of Applied Microbiology; 1998; pp. 865-874.

Mahillon et al.; Microbiology and Molecular Biology Reviews, Sep. 1998, p. 725-774; vol. 62, No. 3.

Kohman; "Cellulose as an Insulating Material"; Industrial and Engineering Chemistry; vol. 31, No. 7; pp. 807 and 810; date unknown but Applicants admit it is prior art.

Dwivedi; et al.; Detection of E. coli Cell Using Capacitance Modulation; Excerpt from the Proceedings of the COMSOL Conference, 2010.

Ah Andeen-Hagerling; product brochure for AH2700A 50 Hz-20kHz Ultra-precision Capacitance Bridge; 2010.

Bio-Rad, Instruction Manual for Gene Pulser MCcell™ ShockPod™ Cuvette Chamber; date unknown but Applicants admit it is prior art.

STERIS Safety Data Sheet for VERIFY@ Spore Test Strip for S40™ Sterilant; 2016.

Kasturirangan, A.; Specific Interactions in Carbon Dioxide + Polymer Systems; Georgia Institute of Technology, Dec. 2007.

Liu et al., "A Survey on Gas Sensing Technology", Sensors, 12, 9635-9665 (2012).

Oberlander et al.; "Study of Interdigitated Electrode Arrays Using Experiments and Finite Element Models for the Evaluation of Sterilization Processes"; Sensors 2015, 15, 26115-26127.

Terzic et al.; "Capacitive Sensing Technology"; A Neural Network to Fluid Quantity Measurement in Dynamic Environments; Jan. 1, 2012; pp. 11-37.

Baxter; "Capacitive Sensors"; Jul. 20, 2000; Retrieved from Internet: URL:http://www.capsense.com/capense-wp.pd.

Horta et al.; "On-Line Monitoring of Biomass Concentration Based on a Capacitance Sensor: Assessing the Methodology for Different Bacteria and yeast High Cell Density Fed-Batch Cultures"; Brazilian Journal of Chemical Engineering; vol. 32, No. 4, Dec. 1, 2015; pp. 821-829.

Stetter; "Amperometric Gas Sensors—A Review"; Chem. Rev. 2008; pp. 352-366.

ZEUS Technical Whitepaper; Dielectric Properties of Polymers; Zeus Industrial Products, Inc.; 2005.

MacDiarmid et al.; "The Concept of 'Doping' of Conducting Polymers: The Role of Reduction Potentials"; Philosophical Transactions of the Royal Society of London, Series A, Mathematical and Physical Sciences, vol. 314, Issue 1528, pp. 3-14.

Toniolo et al.; "Amperometric monitoring of hydrogen peroxide in workplace atmospheres by electrodes supported on ion-exchange membranes"; Journal of Electroanalytical Chemistry 514 (2001), pp. 123-128.

Kuwata et al.; "Detection of gaseous hydrogen peroxide using planar-type amperometric cell at room temperature"; Sensors and Actuators B 65 (2000); pp. 325-326.

Chang; "Amperometric Gas Sensors"; Talanta, vol. 40, No. 4, pp. 461-477; 1993.

Litt; National Science Foundation presentation; "New Polymer Electrolytes"; Nov. 14, 2001.

Gofer et al.; "Electrochemistry in Ultrahigh Vacuum: Intercalation of Lithium into the Basal Plane of Highly Oriented Pyrolytic Graphite from a Poly(ethylene oxide)/LiClO$_4$ Solid Polymer Electrolyte"; The Journal of Physical Chemistry; vol. 99, No. 31, Aug. 3, 1995; pp. 11797-11800.

Gofer et al.; Underpotential Deposition of Lithium of Polycrystalline Gold from a LiClO$_4$/Poly(ethylene oxide) Solid Polymer Electrolyte in Ultrahigh Vacuum; J. Phys. Chem., 1995, 99; pp. 11739-11741.

Wiedemair et al.; "Toward a hydrogen peroxide sensor for exhaled breath analysis"; Procedia Engineering; vol. 25, (2011)Jan. 8, 2012; pp. 116-119.

Lange et al.; "Conducting polymers in chemical sensors and arrays"; Analytica Chimica Acta, Elsevier, Amsterdam, NL; vol. 614, No. 1, Apr. 28, 2008; pp. 1-26.

Miller et al.; "Nanostructured Tin Dioxide Materials for Gas Sensor Applications"; In: "Functional Nanomaterials"; Dec. 31, 2006; America Scientific Publishers; pp. 1-24.

(56) References Cited

OTHER PUBLICATIONS

Pratt; "Applications of Conducting Polymers"; http://homepage.dtn.ntl.com/colin.pratt/applcp.htm; Aug. 18, 2003.
Pratt; "Conducting Polymers"; http://homepage.dtn.ntl.com/colin.pratt/cpoly.htm; Feb. 22, 1996.
International Preliminary Report on Patentability for related International Application No. PCT/US2018/041584 dated Oct. 7, 2019.
International Preliminary Report on Patentability for related International Application No. PCT/US2018/041589 dated Oct. 7, 2019.
International Preliminary Report on Patentability for related International Application No. PCT/US2018/041594 dated Oct. 7, 2019.
Rules 161(1) and 162 EPC Communication for related European Application No. 18752656.1 dated Feb. 21, 2020.
Rules 161(1) and 162 EPC Communication for related European Application No. 18752657.9 dated Feb. 21, 2020.
Rules 161(1) and 162 EPC Communication for related European Application No. 18752658.7 dated Feb. 21, 2020.

\* cited by examiner

PROCESS FOR DETERMINING VIABILITY OF TEST MICROORGANISMS OF BIOLOGICAL INDICATOR AND STERILIZATION DETECTION DEVICE FOR DETERMINING SAME

TECHNICAL FIELD

The present disclosure relates to a process for determining the viability of a biological indicator. A sterilization detection device may utilize said process for evaluating the efficacy of a sterilization process.

BACKGROUND

Biological indicators, which typically include a carrier and test microorganisms (e.g., spores) deposited on the carrier, are used for evaluating the efficacy of sterilization processes. The biological indicator is placed in a sterilization chamber and subjected to a sterilization process along with the load intended for sterilization (e.g., a medical device). Following the sterilization process, the biological indicator is exposed to a growth media and incubated for the purpose of determining if any of the test organisms are viable. A successful sterilization process is indicated by a complete inactivation (no outgrowth) of the test organisms. An unsuccessful sterilization process is indicated by an incomplete inactivation (outgrowth detected) of the test organisms.

SUMMARY OF THE INVENTION

Primarily in the health care industry, but also in many other commercial and industrial applications, it is often necessary to monitor the effectiveness of the processes used to sterilize equipment such as medical and non-medical devices, instruments and other articles and materials. It is often standard practice in these sterilization processes to include a biological indicator in the batch of articles to be sterilized. This allows a direct approach to assay the lethality of the sterilization process.

Methods of sterility assurance typically involve exposing a biological indicator containing one or more test organisms to the sterilization process and then measuring the outgrowth of any surviving test organisms. Sterility may be assured if there is no outgrowth of the test organisms following exposure to the sterilization process. Bacterial spores (e.g., *Geobacillus stearothermophilus, Bacillus subtilis, Bacillus atrophaeus*, and the like) are typically used as the test organisms. Upon completion of the sterilization process, the biological indicator is exposed to an assay medium under conditions that would promote the growth of any surviving test organism cells. The assay medium often contains a chemical dye which changes color in response to actively growing (metabolizing) cells. Because of the requirement for growth and metabolism, the processes employing these test organisms typically require about 24 to 72 hours of incubation before the effectiveness of the sterilization process can be determined. A problem with this process relates to the fact that many users of sterilized articles, such as health care facilities and the like, have limited resources and may reuse the "sterilized" articles within 24 to 72 hours and sometimes immediately. In such settings, the 24 to 72 hour holding period for sterility verification may be impractical, costly and inefficient. Thus, a problem in the art relates to determining the efficacy of a sterilization process within a short period of time.

In accordance with an aspect of the present application, a process for determining the viability of a biological indicator includes: exposing the biological indicator to a viability detection medium, the biological indicator including test microorganisms, the exposing the biological indicator to the viability detection medium producing a gaseous reaction product when one or more of the test microorganisms are viable; and detecting with a sensing device the presence or absence of the gaseous reaction product produced by the biological indicator combined with the viability detection medium, the sensing device including an electro-mechanical sensor, wherein the presence of the gaseous reaction product indicates the presence of viable test microorganisms and the absence of the gaseous reaction product indicates the absence of viable test microorganisms. In an embodiment, the viability detection medium causes viable test microorganisms of the biological indicator to metabolically respond and produce the gaseous reaction product. In an embodiment, the combination of viable test microorganisms of the biological indicator and the viability detection medium produces the gaseous reaction product. In an embodiment, viable test microorganisms of the biological indicator produce a chemical, and combination of the chemical and the viability detection medium produces the gaseous reaction product. In an embodiment, the chemical produced by the biological indicator includes peroxidase. In an embodiment, the viability detection medium includes an assay medium. In an embodiment, the assay medium includes one or more nutrient sources. In an embodiment, the viability detection medium includes hydrogen peroxide. In an embodiment, the electro-mechanical sensor includes a quartz crystal microbalance including a coating on a surface of the substrate configured to absorb the gaseous reaction product produced by the biological indicator. In an embodiment, the sensing device includes an electronic device capable of measuring a change in a frequency of oscillation of the electro-mechanical sensor when the gaseous reaction product interacts with a coating of the electro-mechanical sensor, the change in the frequency indicating the presence of viable test microorganisms. In an embodiment, the coating includes a metal oxide. In an embodiment, the coating includes an inorganic material. In an embodiment, the coating includes an organic material. In an embodiment, the coating includes a polymer. In an embodiment, the coating further includes an additive to increase attraction to the gaseous reaction product or catalyze the gas. In an embodiment, the biological indicator includes bacterial spores. In an embodiment, the biological indicator includes bacteria. In an embodiment, the biological indicator includes bacteria of the *Bacillus* or *Clostridia* genera. In an embodiment, the biological indicator includes *Geobacillus stearothermophilus, Bacillus atrophaeus, Bacillus subtilis, Bacillus pumilus, Bacillus coagulans, Clostridium sporogenes, Bacillus subtilis globigii, Bacillus cereus, Bacillus circulans*, or a mixture of two or more thereof. In an embodiment, the gaseous reaction product includes a volatile organic compound. In an embodiment, the gaseous reaction product includes carbon dioxide. In an embodiment, the gaseous reaction product includes oxygen. In an embodiment, the gaseous reaction product includes methane. In an embodiment, the step of detecting the presence or absence of the gaseous reaction product is conducted under vacuum. In an embodiment, the process further includes exposing the biological indicator to a sterilization medium prior to exposing the biological indicator to the viability detection medium. In an embodiment, the sterilization medium includes steam, dry heat, radiation, plasma, ozone, vaporized hydrogen peroxide, vaporized peracetic acid, chlorine dioxide, one or more gaseous sterilants, and/or one or more liquid sterilants. In an embodiment, the process of further includes the step of heating the biological indicator after the step of exposing the biological indicator to a sterilization medium and prior to the step of exposing the biological indicator to the viability detection medium.

In accordance with another aspect of the present application, a sterilization detection device includes: a container configured to contain a biological indicator including test microorganisms; a viability detection medium arranged to be brought into contact with the biological indicator in the container to cause production of a gaseous reaction product when one or more of the test microorganisms of the biological indicator are viable; and a sensing device disposed in the container and configured to detect the presence or absence of the gaseous reaction product produced by the biological indicator combined with the viability detection medium, the sensing device including an electro-mechanical sensor, wherein the presence of the gaseous reaction product indicates the presence of viable test microorganisms and the absence of the gaseous reaction product indicates the absence of viable test microorganisms. In some embodiments, the viability detection medium causes viable test microorganisms of the biological indicator to metabolically respond and produce the gaseous reaction product. In some embodiments, the combination of viable test microorganisms of the biological indicator and the viability detection medium produces the gaseous reaction product. In some embodiments, viable test microorganisms of the biological indicator produce a chemical, and combination of the chemical and the viability detection medium produces the gaseous reaction product. In some embodiments, the chemical produced by the biological indicator includes peroxidase. In some embodiments, the viability detection medium includes an assay medium. In some embodiments, the assay medium includes one or more nutrient sources. In some embodiments, the viability detection medium includes hydrogen peroxide. In some embodiments, the electro-mechanical sensor includes a quartz crystal microbalance including a coating on a surface of the substrate configured to absorb the gaseous reaction product produced by the biological indicator. In some embodiments, the coating includes a metal oxide. In some embodiments, the coating includes an inorganic material. In some embodiments, the coating includes an organic material. In some embodiments, the coating includes a polymer. In some embodiments, the coating further includes an additive to increase attraction to the gaseous reaction product or catalyze the gas. In some embodiments, the sensing device includes an electronic device configured to measure a change in a frequency of oscillation of the electro-mechanical sensor when the gaseous reaction product interacts with a coating of the electro-mechanical sensor, the change in the frequency indicating the presence of viable test microorganisms. In some embodiments, the biological indicator includes bacterial spores. In some embodiments, the biological indicator includes bacteria. In some embodiments, the biological indicator includes bacteria of the *Bacillus* or *Clostridia* genera. In some embodiments, the biological indicator includes *Geobacillus stearothermophilus, Bacillus atrophaeus, Bacillus subtilis, Bacillus pumilus, Bacillus coagulans, Clostridium sporogenes, Bacillus subtilis globigii, Bacillus cereus, Bacillus circulans*, or a mixture of two or more thereof. In some embodiments, the gaseous reaction product includes a volatile organic compound. In some embodiments, the gaseous reaction product includes carbon dioxide. In some embodiments, the gaseous reaction product includes oxygen. In some embodiments, the gaseous reaction product includes methane. In some embodiments, the sterilization detection device includes a vacuum pump in fluid communication with the container and configured to produce a vacuum within the container.

In accordance with another aspect of the present application, a process for determining the viability of a biological indicator includes: exposing the biological indicator to a sterilization medium, the biological indicator including test microorganisms; subsequently exposing the biological indicator to an assay medium that causes the test microorganisms of the biological indicator when viable to produce a gaseous reaction product; and detecting the presence or absence of a gaseous reaction product produced by the biological indicator exposed to the assay medium using a sensing device, the sensing device including a capacitive sensor, an electro-mechanical sensor, or a resistive sensor, wherein the presence of the gaseous reaction product indicates the presence of viable test microorganisms and the absence of the gaseous reaction product indicates the absence of viable test microorganisms. In an embodiment, the step of detecting the presence or absence of a gaseous reaction product produced by the biological indicator exposed to the assay medium using a sensing device is conducted under vacuum. In an embodiment, the sensing device includes an electro-mechanical sensor. In an embodiment, the electro-mechanical sensor includes a quartz crystal microbalance including a coating on a surface of the substrate configured to absorb or adsorb the gaseous reaction product produced by the biological indicator. In an embodiment, the coating includes a metal oxide. In an embodiment, the coating includes an inorganic material. In an embodiment, the coating includes an organic material. In an embodiment, the coating includes a polymer. In an embodiment, the coating further includes an additive to increase attraction to the gaseous reaction product or catalyze the gas. In an embodiment, the sensing device further includes an electronic device configured to measure a change in a frequency of oscillation of the electro-mechanical sensor when the gaseous reaction product interacts with the coating, the change in the frequency indicating the presence of viable test microorganisms. In an embodiment, the sensing device includes a capacitive sensor including a pair of electrical conductors separated by a dielectric material, the dielectric material configured to absorb or adsorb the gaseous reaction product, the presence of the gaseous reaction product changing the dielectric constant between the electrical conductors. In an embodiment, the dielectric material is a porous material through which the gaseous reaction product diffuses or is a liquid material. In an embodiment, the capacitive sensor is embodied as a parallel plate capacitor, a cylindrical capacitor, or a spherical capacitor. In an embodiment, the sensing device further includes an electronic device configured to measure a change in the capacitance of the capacitive sensor when the gaseous reaction product interacts with the material, the change in the capacitance indicating the presence of viable test microorganisms. In an embodiment, the sensing device includes a resistive sensor including a conductive substrate, the conductive substrate configured to absorb or adsorb the gaseous reaction product, the presence of the gaseous reaction product changing the electrical conductivity of the substrate. In an embodiment, the substrate is a porous material through which the gaseous reaction product diffuses. In an embodiment, the substrate is a conductive substrate and the presence of the gaseous reaction product increases the electrical conductivity of the substrate. In an embodiment, the substrate is a conductive substrate and the presence of the gaseous reaction product decreases the electrical conductivity of the substrate. In an embodiment, the substrate includes a dopant that reacts with the gaseous reaction product and lowers the dopant concentration in the substrate, changing the electrical conductivity of the substrate. In an embodiment, the sensing device further includes an electronic device configured to measure a change in conductivity of the resistive sensor when the gaseous reaction product interacts with the material, the change in the current indicating the presence of viable test microorganisms. In an embodiment, the biological indicator includes bacterial spores. In an embodiment, the step of exposing the bacterial spores to the assay medium causes viable bacterial spores to begin the process of germination. In an embodiment, the biological indicator includes bacteria. In an embodiment, the biological indicator includes bacteria of the *Bacillus* or *Clostridia* genera. In an embodiment, the biological indicator includes *Geobacillus stearothermophilus, Bacillus atrophaeus, Bacillus subtilis, Bacillus pumilus, Bacillus coagulans, Clostridium sporogenes, Bacillus subtilis globigii, Bacillus cereus, Bacillus circulans*, or a mixture of two or more thereof. In an embodiment, the biological indicator includes *Geobacillus stearothermophilus*. In an embodiment, the biological indicator includes *Bacillus atrophaeus*. In an embodiment, the gaseous reaction product includes a volatile organic compound. In an embodiment, the gaseous reaction product includes carbon dioxide. In an embodiment, the gaseous reaction product includes oxygen. In an embodiment, the gaseous reaction product includes methane. In an embodiment, the sterilization medium includes steam, dry heat, radiation, plasma, ozone, vaporized hydrogen peroxide, vaporized peracetic acid, chlorine dioxide, one or more gaseous sterilants, and/or one or more liquid sterilants. In an embodiment, the assay medium includes one or more nutrient sources.

In accordance with another aspect of the present disclosure, a process for determining the viability of a biological indicator includes: exposing the biological indicator to a sterilization medium, the biological indicator including test microorganisms; subsequently exposing the biological indicator to a viability detection medium, the viability detection medium when combined with viable test microorganisms of the biological indicator or with a chemical produced by viable test microorganisms of the biological indicator producing a gaseous reaction product; and detecting with a sensing device the presence or absence of a gaseous reaction product produced by the biological indicator combined with the detection medium or a gaseous reaction product produced by the combination of the chemical produced by the biological indicator and the detection medium, the sensing device including a capacitive sensor, an electro-mechanical sensor, or a resistive sensor, wherein the presence of the gaseous reaction product indicates the presence of viable test microorganisms and the absence of the gaseous reaction product indicates the absence of viable test microorganisms. In an embodiment, the step of detecting the presence or absence of a gaseous reaction product produced by the biological indicator exposed to the viability detection medium using a sensing device is conducted under vacuum. In an embodiment, the viability detection medium includes liquid hydrogen peroxide. In an embodiment, the gaseous reaction product includes oxygen. In an embodiment, the chemical produced by the biological indicator includes the enzyme peroxidase. In an embodiment, the chemical produced by the biological indicator includes the enzyme catalase. In an embodiment, the process further includes the step of heating the biological indicator after the step of exposing the biological indicator to a sterilization medium and prior to the step of exposing the biological indicator to the viability detection medium. In an embodiment, the sensing device includes an electro-mechanical sensor. In an embodiment, the electro-mechanical sensor includes a quartz crystal microbalance including a coating on a surface of the substrate configured to absorb the gaseous reaction product produced by the biological indicator. In an embodiment, the sensing device includes: an electronic device capable of measuring a change in a frequency of oscillation of the electro-mechanical device when the gaseous reaction product interacts with the coating, the change in the frequency indicating the presence of viable test microorganisms. In an embodiment, the coating includes a metal oxide. In an embodiment, the coating includes an inorganic material. In an embodiment, the coating includes an organic material. In an embodiment, the coating includes a polymer. In an embodiment, the coating further includes an additive to increase attraction to the gaseous reaction product or catalyze the gas. In an embodiment, the sensing device includes a capacitive sensor including a pair of electrical conductors. In an embodiment, the sensing device includes a capacitive sensor including a pair of electrical conductors separated by a dielectric material, the dielectric material configured to absorb or adsorb the gaseous reaction product, the presence of the gaseous reaction product changing the dielectric constant between the electrical conductors. In an embodiment, the dielectric material is air. In an embodiment, the dielectric material is a porous material through which the gaseous reaction product diffuses. In an embodiment, the capacitive sensor is embodied as a parallel plate capacitor, a cylindrical capacitor, or a spherical capacitor. In an embodiment, the sensing device further includes an electronic device configured to measure a change in the capacitance of the capacitive sensor when the gaseous reaction product interacts with the material, the change in the capacitance indicating the presence of viable test microorganisms. In an embodiment, the sensing device includes a resistive sensor including a conductive substrate, the conductive substrate configured to absorb or adsorb the gaseous reaction product, the presence of the gaseous reaction product changing the electrical conductivity of the substrate. In an embodiment, the substrate is a porous material through which the gaseous reaction product diffuses. In an embodiment, the substrate is a conductive substrate and the presence of the gaseous reaction product increases the electrical conductivity of the substrate. In an embodiment, the substrate is a conductive substrate and the presence of the gaseous reaction product decreases the electrical conductivity of the substrate. In an embodiment, the substrate includes a dopant that reacts with the gaseous reaction product and lowers the dopant concentration in the substrate, changing the electrical conductivity of the substrate. In an embodiment, the sensing device further includes an electronic device configured to measure a change in conductivity of the resistive sensor when the gaseous reaction product interacts with the material, the change in the current indicating the presence of viable test microorganisms. In an embodiment, the biological indicator includes bacterial spores. In an embodiment, the biological indicator includes bacteria. In an embodiment, the biological indicator includes bacteria of the *Bacillus* or *Clostridia* genera. In an embodiment, the biological indicator includes *Geobacillus stearothermophilus, Bacillus atrophaeus, Bacillus subtilis, Bacillus pumilus, Bacillus coagulans, Clostridium sporogenes, Bacillus sub-*

*tilis globigii*, *Bacillus cereus*, *Bacillus circulans*, or a mixture of two or more thereof. In an embodiment, the biological indicator includes *Geobacillus stearothermophilus*. In an embodiment, the biological indicator includes *Bacillus atrophaeus*. In an embodiment, the sterilization medium includes steam, dry heat, radiation, plasma, ozone, vaporized hydrogen peroxide, vaporized peracetic acid, chlorine dioxide, one or more gaseous sterilants, and/or one or more liquid sterilants.

In accordance with another aspect of the present disclosure, a sterilization detection device includes: a container configured to contain a biological indicator including test microorganisms; an assay medium arranged to be brought into contact with the biological indicator within the container that causes test microorganisms of the biological indicator when viable to produce a gaseous reaction product; and a sensing device disposed in the container and configured to detect the presence or absence of a gaseous reaction product produced by the biological indicator exposed to the assay medium using a sensing device, the sensing device including a capacitive sensor, an electro-mechanical sensor, or a resistive sensor, wherein the presence of the gaseous reaction product indicates the presence of viable test microorganisms and the absence of the gaseous reaction product indicates the absence of viable test microorganisms. In an embodiment, the sterilization detection device further includes a vacuum pump in fluid communication with the container and configured to produce a vacuum within the container. In an embodiment, the sensing device includes an electro-mechanical sensor. In an embodiment, the electro-mechanical sensor includes a quartz crystal microbalance including a coating on a surface of the substrate configured to absorb the gaseous reaction product produced by the biological indicator. In an embodiment, the coating includes a metal oxide. In an embodiment, the coating includes an inorganic material. In an embodiment, the coating includes an organic material. In an embodiment, the coating includes a polymer. In an embodiment, the coating further includes an additive to increase attraction to the gaseous reaction product or catalyze the gas. In an embodiment, the sensing device includes an electronic device configured to measure a change in a frequency of oscillation of the electro-mechanical device when the gaseous reaction product interacts with the coating, the change in the frequency indicating the presence of viable test microorganisms. In an embodiment, the sensing device includes a capacitive sensor including a pair of electrical conductors separated by a dielectric material, the dielectric material configured to absorb or adsorb the gaseous reaction product, the presence of the gaseous reaction product changing the dielectric constant between the electrical conductors. In an embodiment, the dielectric material is a porous material configured for diffusion of the gaseous reaction product therethrough or is a liquid material. In an embodiment, the capacitive sensor is embodied as a parallel plate capacitor, a cylindrical capacitor, or a spherical capacitor. In an embodiment, the sensing device further includes an electronic device configured to measure a change in the capacitance of the capacitive sensor when the gaseous reaction product interacts with the material, the change in the capacitance indicating the presence of viable test microorganisms. In an embodiment, the sensing device includes a resistive sensor including a conductive substrate, the conductive substrate configured to absorb or adsorb the gaseous reaction product, the presence of the gaseous reaction product changing the electrical conductivity of the substrate. In an embodiment, the substrate is a porous material configured for diffusion of the gaseous reaction product therethrough. In an embodiment, the substrate is a conductive substrate and the presence of the gaseous reaction product increases the electrical conductivity of the substrate. In an embodiment, the substrate is a conductive substrate and the presence of the gaseous reaction product decreases the electrical conductivity of the substrate. In an embodiment, the substrate includes a dopant that reacts with the gaseous reaction product and lowers the dopant concentration in the substrate, changing the electrical conductivity of the substrate. In an embodiment, the sensing device further includes an electronic device configured to measure a change in conductivity of the resistive sensor when the gaseous reaction product interacts with the material, the change in the current indicating the presence of viable test microorganisms. In an embodiment, the biological indicator includes bacterial spores. In an embodiment, the biological indicator includes bacteria. In an embodiment, the biological indicator includes bacteria of the *Bacillus* or *Clostridia* genera. In an embodiment, the biological indicator includes *Geobacillus stearothermophilus*, *Bacillus atrophaeus*, *Bacillus subtilis*, *Bacillus pumilus*, *Bacillus coagulans*, *Clostridium sporogenes*, *Bacillus subtilis globigii*, *Bacillus cereus*, *Bacillus circulans*, or a mixture of two or more thereof. In an embodiment, the biological indicator includes *Geobacillus stearothermophilus*. In an embodiment, the biological indicator includes *Bacillus atrophaeus*. In an embodiment, the gaseous reaction product includes a volatile organic compound. In an embodiment, the gaseous reaction product includes carbon dioxide. In an embodiment, the gaseous reaction product includes oxygen. In an embodiment, the gaseous reaction product includes methane. In an embodiment, the assay medium includes one or more nutrient sources. In an embodiment, a process for determining the viability of a biological indicator includes: exposing a biological indicator to a sterilization medium; and determining the viability of the biological indicator using the sterilization detection device by bringing the biological indicator into contact with the assay medium within the container and detecting the presence or absence of the gaseous reaction product. In an embodiment, the biological indicator and/or the detection medium is added to the container subsequent to being exposed to the sterilization medium. In an embodiment, the biological indicator and/or the detection medium is added to the container prior to being exposed to the sterilization medium. In an embodiment, the sterilization medium includes steam, dry heat, radiation, plasma, ozone, vaporized hydrogen peroxide, vaporized peracetic acid, chlorine dioxide, one or more gaseous sterilants, and/or one or more liquid sterilants.

In accordance with another aspect of the present disclosure, a sterilization detection device includes: a container configured to contain a biological indicator including test microorganisms; a viability detection medium arranged to be brought into contact with the biological indicator or with a chemical produced by viable test microorganisms of the biological indicator within the container to produce a gaseous reaction product; and a sensing device disposed in the container and configured to detect the presence or absence of a gaseous reaction product produced by the biological indicator combined with the detection medium or a gaseous reaction product produced by the combination of the chemical produced by the biological indicator and the detection medium, the sensing device including a capacitive sensor, an electro-mechanical sensor, or a resistive sensor, wherein the presence of the gaseous reaction product indicates the presence of viable test microorganisms and the absence of the gaseous reaction product indicates the absence of viable test microorganisms. In an embodiment, the sterilization detection device further includes a vacuum pump in fluid communication with the container and configured to produce a vacuum within the container. In an embodiment, the viability detection medium includes hydrogen peroxide. In an embodiment, the gaseous reaction product includes oxygen. In an embodiment, the chemical produced by the biological indicator includes peroxidase. In an embodiment, the sensing device includes an electro-mechanical sensor. In an embodiment, the electro-mechanical sensor includes a quartz crystal microbalance including a coating on a surface of the substrate configured to absorb the gaseous reaction product produced by the biological indicator. In an embodiment, the coating includes a metal oxide. In an embodiment, the coating includes an inorganic coating. In an embodiment, the coating includes an organic coating. In an embodiment, the coating includes a polymer. In an embodiment, the coating further includes an additive to increase attraction to the gaseous reaction product or catalyze the gas. In an embodiment, the sensing device includes an electronic device configured to measure a change in a frequency of oscillation of the electro-mechanical device when the gaseous reaction product interacts with the coating, the change in the frequency indicating the presence of viable test microorganisms. In an embodiment, the sensing device includes a capacitive sensor including a pair of electrical conductors separated by a dielectric material, the dielectric material configured to absorb or adsorb the gaseous reaction product, the presence of the gaseous reaction product changing the dielectric constant between the electrical conductors. In an embodiment, the dielectric material is a porous material configured for diffusion of the gaseous reaction product therethrough. In an embodiment, the capacitive sensor is embodied as a parallel plate capacitor, a cylindrical capacitor, or a spherical capacitor. In an embodiment, the sensing device further includes an electronic device configured to measure a change in the capacitance of the capacitive sensor when the gaseous reaction product interacts with the material, the change in the capacitance indicating the presence of viable test microorganisms. In an embodiment, the sensing device includes a resistive sensor including a conductive substrate, the conductive substrate configured to absorb or adsorb the gaseous reaction product, the presence of the gaseous reaction product changing the electrical conductivity of the substrate. In an embodiment, the substrate is a porous material configured for diffusion of the gaseous reaction product therethrough. In an embodiment, the substrate is a conductive substrate and the presence of the gaseous reaction product increases the electrical conductivity of the substrate. In an embodiment, the substrate is a conductive substrate and the presence of the gaseous reaction product decreases the electrical conductivity of the substrate. In an embodiment, the substrate includes a dopant that reacts with the gaseous reaction product and lowers the dopant concentration in the substrate, changing the electrical conductivity of the substrate. In an embodiment, the sensing device further includes an electronic device configured to measure a change in conductivity of the resistive sensor when the gaseous reaction product interacts with the material, the change in the current indicating the presence of viable test microorganisms. In an embodiment, the biological indicator includes bacterial spores. In an embodiment, the biological indicator includes bacteria. In an embodiment, the biological indicator includes bacteria of the *Bacillus* or *Clostridia* genera. In an embodiment, the biological indicator includes *Geobacillus stearothermophilus, Bacillus atrophaeus, Bacillus subtilis, Bacillus pumilus, Bacillus coagulans, Clostridium sporogenes, Bacillus subtilis globigii, Bacillus cereus, Bacillus circulans*, or a mixture of two or more thereof. In an embodiment, the biological indicator includes *Geobacillus stearothermophilus*. In an embodiment, the biological indicator includes *Bacillus atrophaeus*. In an embodiment, a process for determining the viability of a biological indicator includes: exposing a biological indicator to a sterilization medium; and determining the viability of the biological indicator using the sterilization detection device by bringing the biological indicator into contact with the viability detection medium within the container and detecting the presence or absence of the gaseous reaction product. In an embodiment, the biological indicator is added to the container subsequent to being exposed to the sterilization medium. In an embodiment, the biological indicator is added to the container prior to being exposed to the sterilization medium. In an embodiment, the sterilization medium includes steam, dry heat, radiation, plasma, ozone, vaporized hydrogen peroxide, vaporized peracetic acid, chlorine dioxide, one or more gaseous sterilants, and/or one or more liquid sterilants.

With the processes and sterilization detection devices of the present disclosure, it is possible to determine whether live test microorganisms or spores of a biological indicator are present after the biological indicator has been subjected to a sterilization. The time in which this determination can be made may be reduced as compared with typical methods of sterility assurance. In some embodiments, determination of whether live test microorganisms or spores are present can be determined instantaneously, or within a period of time of up to about 2000 seconds, or up to about 1500 seconds, or up to about 1000 seconds, or up to about 500 seconds, or up to about 200 seconds, or up to about 100 seconds, or up to about 50 seconds, or up to about 30 seconds, or in the range from about 5 to about 2000 seconds, or from about 10 to about 1800 seconds, or from about 20 to about 1500 seconds, or from about 30 to about 1200 seconds, or from about 50 to about 1000 seconds, or from about 60 to about 800 seconds.

BRIEF DESCRIPTION OF THE DRAWINGS

In the annexed drawings, like parts and features have like designations.

DETAILED DESCRIPTION

Figure 1:
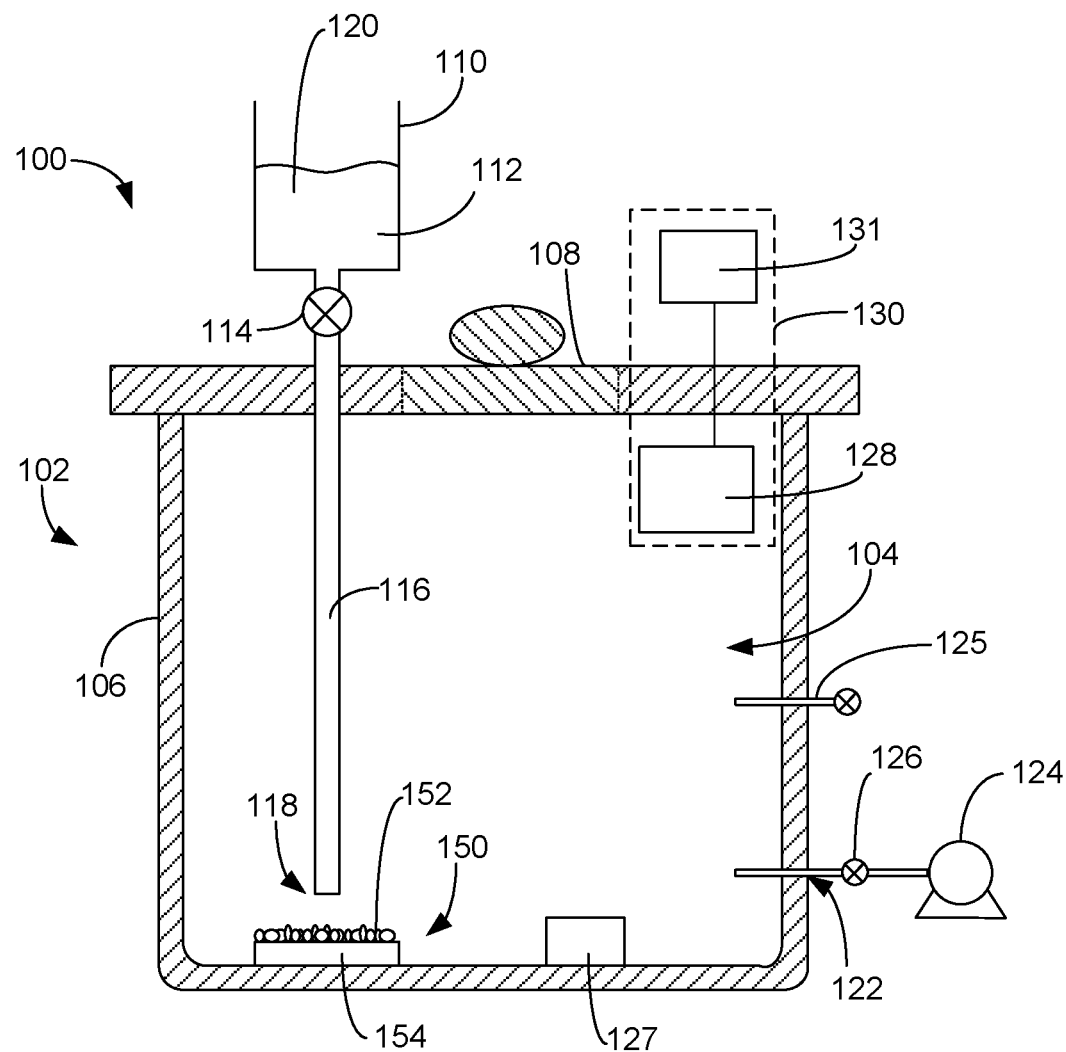
FIG. 1 is a schematic diagram of an exemplary sterilization detection device.

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The phrase "and/or" should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The word "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," may refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The transitional words or phrases, such as "comprising," "including," "carrying," "having," "containing," "involving," "holding," and the like, are to be understood to be open-ended, i.e., to mean including but not limited to.

The term "capacitor" refers to a two-terminal electrical component used to store electrical energy temporarily. The capacitor provided by the present disclosure includes two electrical conductors separated by a dielectric.

The term "dielectric" refers to an electrical insulator that can be polarized by an applied electrical field. When a dielectric is placed in an electrical field, electric charges do not flow through the material as they do in a conductor, but only slightly shift from their average equilibrium positions causing dielectric polarization.

The term "resistor" refers to a two-terminal electrical component that implements electrical resistance. The resistor provided by the present disclosure includes electrical conductors separated by a substrate, or separated by a substrate and one or more additional layers.

The term "biological indicator" refers to an article that can be used to determine the efficacy of a sterilization process. The biological indicator may include test microorganisms. The term "test microorganism" may refer to a microorganism that is more resistant to a sterilization process than the organisms intended for destruction during the sterilization process. In theory, if the test microorganisms were to die during the sterilization process, then all organisms intended for destruction during the sterilization process that were less resistant to the sterilization than the test microorganisms would also die. The test microorganisms may include a bacteria. The test microorganisms may include spores. The test microorganisms may include bacterial spores. The biological indicator may include the test microorganisms (e.g., bacteria, spores or bacterial spores) on a carrier. The biological indicator may include bacteria, the bacteria may be present within a defined space or deposited on a carrier. The biological indicator may include spores (e.g., bacterial spores), the spores may be present within a defined space or on a carrier. The biological indicator may include a spore strip.

The term "bacteria" refers to a domain of prokaryotic microorganisms.

The term "spore" refers to a unit of asexual reproduction that may be adapted for dispersal and survival for extended periods of time under unfavorable conditions. Spores are highly resistant, dormant cell types. Endospores (or simply spores) form within the vegetative mother cell in response to adverse changes in the environment, most commonly nutrient depletion. The mother cell undergoes an asymmetrical cell division, where it replicates its genetic material, which is then surrounded by multiple concentric and spore specific layers. The mother cell then disintegrates, releasing the mature dormant spore which requires neither nutrients, water nor air for survival and is protected against a variety of trauma, including extremes of temperature, radiation, and chemical assault.

The term "bacterial spore" refers to a spore produced by bacteria.

The term "carrier" refers to a support onto which test microorganisms or spores are deposited to form a biological indicator.

The term "killing" test microorganisms or spores refers to rendering test microorganisms or spores incapable of reproduction, metabolism and/or growth. The term "dead" test microorganisms or spores refers to spores which have been rendered incapable of reproduction, metabolism and/or growth. The test microorganisms or spores used with the biological indicator are selected from those that would be more resistant to a sterilization process for which they are intended to monitor than the organisms to be killed by the sterilization process. The killing of the test microorganisms or spores on the biological indicator during the sterilization process is indicative of a successful sterilization process.

The term "live" test microorganisms or spores refers to test microorganisms or spores that are capable of reproduction, metabolism and/or growth.

The term "sterilization" may be used to refer to a process wherein there is a total absence of living test microorganisms remaining after the sterilization process has been completed. However, processes that are less rigorous than sterilization processes including, for example, disinfection, sanitization, decontamination, cleaning processes, and the like, may be of value in that they significantly reduce the total number of viable organisms and are taken into account with the present disclosure. Unless otherwise indicated, the term "sterilization" is used herein to refer to sterilization processes as well as less rigorous processes such as disinfection, sanitation, decontamination, cleaning, and the like.

The term "sterilant" refers to any medium or energy that can be used to sterilize a substrate (e.g., a medical device, the interior of a room, etc.). The sterilant may include a liquid or a gas. The sterilant may include vaporous hydrogen peroxide, steam, ethylene oxide, peracetic acid, ozone, or a combination of two or more thereof. The sterilant may include ultraviolet light or radiation. The radiation may include x-ray radiation, gamma radiation, or electron beam radiation.

The term "vacuum" is used herein to refer to a pressure that is below atmospheric pressure. The term "vacuum" as used herein therefore includes partial vacuum. The pressure, in terms of absolute pressure, in the vacuum may be in the range from about 0.1 to about 750 Torr, or from about 0.1 to about 700 Torr, or from about 0.1 to about 600 Torr, or from about 0.1 to about 500 Torr, or from about 0.1 to about 400 Torr, or from about 0.1 to about 300 Torr, or from about 0.1 to about 200 Torr, or from about 0.1 to about 100 Torr, or from about 1 to about 75 Torr, or from about 1 to about 50 Torr, or from about 1 to about 25 Torr, or from about 3 to about 25 Torr, or from about 5 to about 25 Torr, or from about 5 Torr to about 20 Torr.

Referring now to the drawings, and with initial reference to FIG. 1, an exemplary sterilization detection device is shown at 100. The sterilization detection device 100 includes a container 102 configured to contain a biological indicator 150. The container 102 includes an interior volume 104 that is suitable for housing the biological indicator 150. The container 102 may be formed by one or more components. In the example shown, the container 102 includes a main body 106 and a lid 108. The lid 108 is removable and may provide access to the interior volume 104 of the container 102. In other exemplary embodiments, an access panel (not shown) may be provided in the main body 106 of the container 102 in addition to or in place of the lid 108. With the lid 108 (and/or access panel) closed, the container 102 may isolate the biological indicator 150 from the outside environment.

The sterilization detection device 100 includes a liquid dispenser 110. In the example shown, the liquid dispenser 110 is embodied as a dropper that includes a reservoir 112, valve 114, and tube 116 having an end 118 that is proximate the location of the biological indicator 150 when the biological indicator is inserted in the interior volume 104 of the container 102. The reservoir may be configured to hold a liquid medium 120, and a predetermined amount of the liquid medium 120 may be dispensed from the reservoir 112 to the tube 116 via valve 114. The dispensed liquid medium 120 may exit the end 118 of the tube 116, where it may be brought into contact with the biological indicator 150. In other embodiments, the liquid disperser may have another suitable configuration for introducing the liquid medium 120 to the biological indicator 150.

The liquid medium 120 may be a viability detection medium that may be brought into contact with the test microorganisms of the biological indicator 150 and/or with a chemical produced by viable test microorganisms of the biological indicator 150. In some embodiments, the viability detection medium is an assay medium that causes the biological indicator 150 including one or more viable test microorganisms 152 (e.g., viable bacterial and bacterial spores) to produce a gaseous reaction product (e.g., as a result of metabolic activity and/or growth of the viable test microorganisms). In an example, the assay medium may include one or more nutrient sources. Exposing the viable test microorganisms 152 of the biological indicator 150 to the assay medium may cause the viable test microorganisms 152 to metabolically respond and ultimately germinate (e.g., and produce vegetative bacteria). This metabolic activity preceding or occurring during the initiation of germination may result in the production of a gaseous reaction product including one or more components (e.g., carbon dioxide, oxygen, nitrogen, hydrogen, hydrogen sulfide, ammonia, methane, and/or one or more volatile organic compounds) that may be used in the determination of the presence of viable test microorganisms 152. An exemplary composition of a gaseous reaction product produced as a result of the reaction of viable test microorganisms with an assay medium is a biogas such as that set forth below in Table 1. In some embodiments, one or more of the exemplary produced compounds of the biogas described in Table 1 may be used in the determination of the presence of viable test microorganisms. Alternatively, if the test microorganisms of the biological indicator are not viable, metabolism and germination may not result and the gaseous reaction product may not be produced.

TABLE 1

Exemplary gaseous reaction product composition

| Compound | % |
|---|---|
| Methane | 50-75 |
| Carbon Dioxide | 25-50 |
| Nitrogen | 0-10 |
| Hydrogen | 0-3 |
| Hydrogen Sulfide | 0-3 |
| Oxygen | 0-3 |

In other embodiments, the viability detection medium is another medium (e.g., hydrogen peroxide) that may be brought into contact with the test microorganisms of the biological indicator 150 and/or with a chemical produced by viable test microorganisms of the biological indicator 150 to generate a gaseous reaction product. As an example, the chemical produced by viable test microorganisms may be one or more enzymes such as one or more peroxidases. One exemplary peroxidase is catalase. Exposing the viable test microorganisms of the biological indicator 150 and/or the chemical produced by the viable test microorganisms 152 of the biological indicator 150 to the viability detection medium may result in the production of a gaseous reaction product (e.g., carbon dioxide, oxygen, methane, and/or one or more volatile organic compounds) that may be used in the determination of the presence of viable test microorganisms 152. As an example, the viability detection medium may include hydrogen peroxide. Contact of the hydrogen peroxide with the viable test microorganisms and/or peroxidase (e.g., catalase) may result in the generation of gaseous reaction product including one or more compounds (e.g., oxygen) that may be used in the determination of the presence of viable test microorganisms 152. Alternatively, if the test microorganisms of the biological indicator are not viable, contact of the hydrogen peroxide with the viable test microorganisms and/or peroxidase (e.g., catalase) may not result in the generation of gaseous reaction product that may be used in the determination of the presence of viable test microorganisms 152.

In some embodiments, the sterilization detection device 100 includes a vacuum port 122. The vacuum port 122 may be coupled to a vacuum pump 124. A valve 126 may be coupled to the vacuum port 122 and may provide for fluid communication between the vacuum pump 124 and the interior volume 104 of the container 102. The vacuum pump 124 may provide a vacuum within the container.

In some embodiments, the sterilization device 100 includes one or more ports 125 into the interior volume 104 of the container 102. The port 125 may be coupled to a gas source and may allow for the controlled introduction of the gas (e.g., oxygen) into the interior volume of the container 102. As an example, in embodiments where a vacuum is provided within the container, an amount of oxygen sufficient to encourage growth of any viable biological indicator may be introduced to the interior volume 104 via the port 125. The added oxygen may provide the viable biological indicator with an atmosphere including oxygen (e.g., for those microorganisms that grow aerobically). And by keeping the pressure within the container below atmospheric pressure, the detection of any gaseous reaction product produced by viable biological indicator may be improved.

In some embodiments, the sterilization device 100 includes a heating element 127. The heating element may be an electrical heating element (e.g., a resister coil or other suitable heating element). The heating element may be controlled (e.g., by the control unit 142) to heat the interior volume 104 of the sterilization device 100 and/or one or more items within the interior volume 104 of the sterilization device 100. In some embodiments, the biological indicator 150 may include bacteria or spores that metabolize and/or germinate at elevated temperatures (e.g., 30° C.-80° C.) that are above room temperature (23° C.). The heating element 127 may allow for the biological indicator 150 to be incubated at an appropriate temperature. The heating element 127 is schematically shown in FIG. 1 as adjacent the biological indicator, although in other embodiments the heating element 127 may be provided in any suitable location (e.g., under the biological indicator).

The sterilization detection device 100 includes a sensing device 128 disposed in the interior volume 104 of the container 102. The sensing device 128 may be part of a gas detection assembly 130 configured to detect the presence or absence of a gaseous reaction product produced by the viable test microorganisms 152 of the biological indicator 150 exposed to the viability detection medium using a sensing device, and/or to detect the presence or absence of a gaseous reaction product produced by the viable test microorganisms 152 of the biological indicator 150 combined with the viability detection medium or a gaseous reaction product produced by the combination of the chemical produced by the viable test microorganisms 152 of the biological indicator 150 and the viability detection medium. The presence of the gaseous reaction product may indicate the presence of viable test microorganisms 152 of the biological indicator 150 and the absence of the gaseous reaction product may indicate the absence of viable test microorganisms 152 of the biological indicator 150. In some embodiments, the sensing device 128 is a capacitive sensor. In some embodiments, the sensing device 128 is an electro-mechanical sensor. In some embodiments, the sensing device 128 is a resistive sensor. In some embodiments, the sensing device 128 includes a combination of a capacitive sensor, an electro-mechanical sensor, and/or a resistive sensor (e.g., a capacitive sensor and an electro-mechanical sensor; a capacitive sensor and a resistive sensor; an electro-mechanical sensor and a resistive sensor; a capacitive sensor, an electro-mechanical sensor, and a resistive sensor). Exemplary embodiments of the sensing device 128 and gas detection assembly 130 are described in more detail below.

The biological indicator 150 may include test microorganisms 152 deposited on a carrier 154. In some embodiments, the test microorganisms 152 may be embodied as bacteria. In some embodiments, the test microorganisms 152 may be embodied as bacterial spores. The test microorganism population for the biological indicator may be in the range from about 500,000 to about 4,000,000 colony forming units (cfu), or from about 500,000 to about 2,500,000 cfu, or from about 500,000 to about 1,500,000 cfu, or from about 750,000 to about 1,200,000 cfu, or about $10^6$ cfu. The spore population for the biological indicator may be in the range from about 500,000 to about 4,000,000 spores, or from about 500,000 to about 2,500,000 spores, or from about 500,000 to about 1,500,000 spores, or from about 750,000 to about 1,200,000 spores. The spore population may be about $10^6$ spores. In other embodiments, the spore population may exceed $10^6$ spores. In an example, the spore population may be in a range from about $2 \times 10^6$ to $10^8$ spores.

The biological indicator 150 may include bacteria or spores (bacterial spores) of the *Bacillus* or *Clostridia* genera that may be used as test microorganisms 152. The spores may be spores of *Geobacillus stearothermophilus*, *Bacillus atrophaeus*, *Bacillus sphaericus*, *Bacillus anthracis*, *Bacillus subtilis*, *Bacillus pumilus*, *Bacillus coagulans*, *Clostridium sporogenes*, *Clostridium difficile*, *Clostridium botulinum*, *Bacillus subtilis globigii*, *Bacillus cereus*, *Bacillus circulans*, or a combination of two or more thereof. The spores may include spores of *Geobacillus stearothermophilus*, *Bacillus atrophaeus*, or a combination thereof.

The carrier 154 may include a strip, sheet or film of any material that does not dissolve or deteriorate during the sterilization processes. The carrier 154 may include a paper strip, e.g., a cellulose strip, or a plastic sheet or film. The plastic may include a polyolefin, polystyrene, polycarbonate, polymethacrylate, polyacrylamide, polyimide, polyester, or a combination of two or more thereof. The carrier 154 may include glass, ceramics, metal foil, or a combination of two or more thereof. The carrier may have a length in the range of about 1 to about 5 cm, or about 2 to about 4 cm; a width in the range from about 0.1 to about 1 cm, or about 0.4 to about 0.7 cm; and a thickness in the range from about 0.2 to about 3 mm, or from about 0.5 to about 1.5 mm. The biological indicator 150 may be referred to as a spore test strip.

The biological indicator 150 may include a commercially available spore test strip. These may include *Geobacillus stearothermophilus* test strips for use in monitoring steam sterilizations; *Bacillus atrophaeus* test strips for monitoring ethylene oxide and dry heat sterilizations; *Bacillus pumilus* test strips for irradiation sterilizations; combined species spore test strips, *G. stearothermophilus* and *B. atrophaeus*, for monitoring steam, ethylene oxide and dry heat sterilizations; and the like. These test strips may be characterized by spore populations in the range from about 500,000 to about 4,000,000 spores, or from about 500,000 to about 2,500,000 spores, or from about 500,000 to about 1,500,000 spores, or from about 750,000 to about 1,200,000 spores per test strip, or about $10^6$ spores per test strip.

The biological indicator 150 may include a VERIFY® Spore Test Strip for 540® Sterilant Concentrate supplied by STERIS Corporation. This test strip may be used for monitoring liquid chemical sterilizations, e.g., peracetic acid sterilizations. These test strips are characterized by spore populations of at least about $10^5$ Geobacillus stearothermophilus spores per test strip.

The biological indicator 150 may be subjected to a sterilization process. The sterilization process may employ any suitable sterilant. Exemplary sterilization medium includes steam, dry heat, radiation, plasma, ozone, vaporized hydrogen peroxide, vaporized peracetic acid, chlorine dioxide, one or more gaseous sterilants, and/or one or more liquid sterilants. The sterilization process may be conducted for an effective period of time to achieve at least a 4 log reduction, or at least a 5 log reduction, or at least a 6 log reduction in the number of test microorganisms, bacteria or spores capable of reproduction, metabolism and/or growth. When at least a 6 log reduction is achieved, the process may be referred to as a sterilization process. When a 4 log reduction or a 5 log reduction is achieved, the process may be considered to be less rigorous than a sterilization process, but nevertheless useful for various disinfection, sanitization, decontamination and/or cleaning applications.

In some embodiments, the biological indicator 150 is added to the interior volume of the container subsequent to being exposed to the sterilization medium. As an example, the biological indicator 150 may be subjected to a sterilization process in a different vessel (not shown) such as a container that substantially encapsulates the test microorganisms. A tortuous path may be provided by the vessel between the test microorganisms or spores and the external environment. The effectiveness of the sterilization process may be tested by treating the test microorganisms 154 of the biological indicator 150 with the sterilant in the same manner as the load being sterilized. The sterilant flows along the tortuous path to the biological indicator 150 where the sterilant flows over and among the test microorganisms 152. After completion of a sterilization process, the biological indicator 150 may be placed in the container 102 of the sterilization detection device 100 and subjected to a process for determining the viability of the test microorganisms 152 of the biological indicator 150. In some embodiments, the biological indicator 150 is removed from the vessel used during the sterilization process prior to insertion into the container 102. In some embodiments, the biological indicator 150 is maintained in the vessel used during the sterilization process and is placed in the container 102 for conducting the process of determining the viability of the test microorganisms 152 of the biological indicator 150.

In some embodiments, the biological indicator 150 is added to the container 102 prior to being exposed to the sterilization medium. This is exemplified in FIGS. 2A and 2B, which show another exemplary embodiment of a sterilization detection device at 200. The exemplary sterilization detection device 200 is provided in a form of a vessel that may itself be subjected to a sterilization process. The sterilization detection device 200 includes a container 102 that includes a main body 106 and a lid 108. The container 102 includes an interior volume 104 including a first compartment 104A, a second compartment 104B, and a third compartment 104C. The first compartment 104A holds the biological indicator 150. The second compartment 104B holds a frangible ampoule 160 that contains the liquid medium 120 (e.g., viability detection medium). The frangible ampoule 160 may be a glass ampoule. The third compartment 104C holds the sensing device 128. A tortuous path 170 is formed by an opening 164 between the lid 108 and the main body 106 through which sterilant gas may enter (e.g., during a sterilization process). The sterilant gas that enters the interior volume 104 may flow through one or more holes 172 that connect the second and third compartments 104B, 104C to the first compartment 104A. The lid 108 is movable with respect to the main body 106 to open and block the tortuous path from the external environment.

The lid includes a protrusion 162 that is configured to assert a force against the ampoule 160 when the lid is closed. Assertion of the force may break the ampoule 160 (FIG. 2B), resulting in release of the liquid medium 120.

As shown, the sensing device 128 is included as part of the gas detection assembly 130. In some embodiments, the lid may include one or more connectors 129 that may allow for the sensing device 128 to be removed from the remainder of the gas detection assembly 130. This may allow, for example, for the sterilization process to be conducted without the entire gas detection assembly 130 being connected to the housing 102. Subsequent to the sterilization process, the remainder of the gas detection assembly 130 can be connected to the sensing device 128 via the one or more connectors 129, and the gas detection process can be conducted. In other embodiments, the sensing device 128 may be connected to the remainder of the gas detection assembly 130 during the sterilization process.

In some embodiments, the sterilization detection device 200 includes a vacuum port 122. The vacuum port 122 may be removably coupled to a vacuum pump. A valve 126 may be coupled to the vacuum port 122 and may provide for fluid communication between the vacuum pump and the interior volume of the container.

In some embodiments, the sterilization device 200 includes one or more ports 125 into the interior volume 104 of the container 102 (e.g., for providing a controlled introduction of gas (e.g., oxygen) into the interior volume, similar to that described in connection with the device shown in FIG. 1). In some embodiments, the sterilization detection device 200 may include a heating element 127.

Figure 2A:
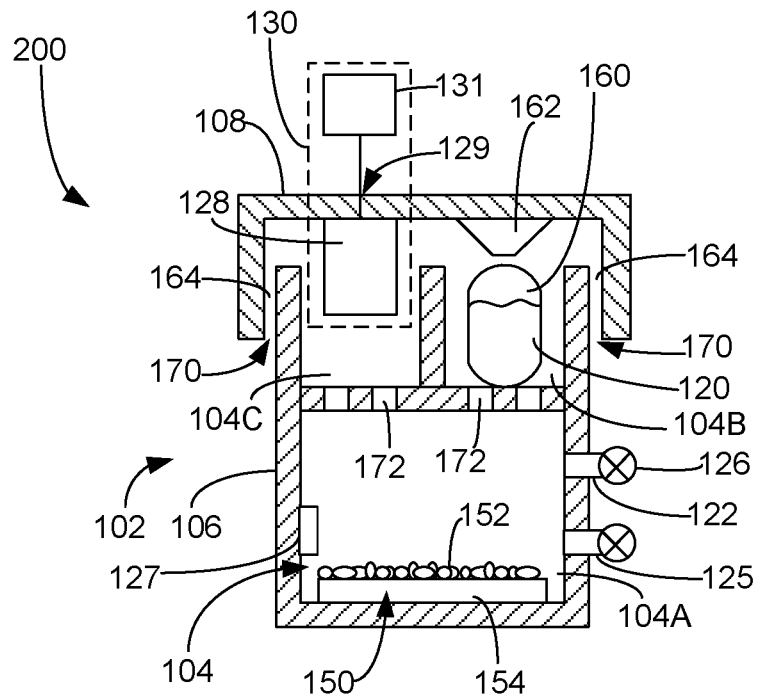
FIGS. 2A and 2B are a schematic diagrams of an exemplary sterilization detection device.
Figure 2B:
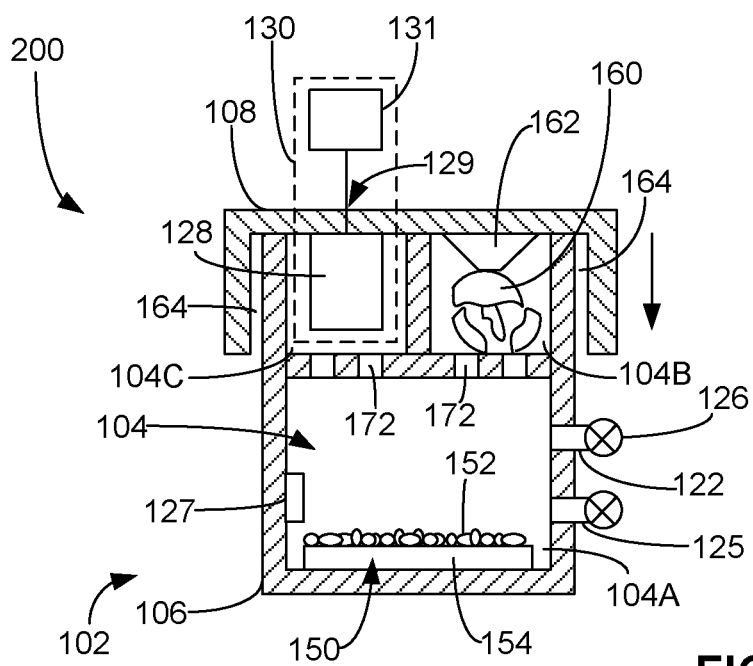

When used in a sterilization process, the lid 108 is held in an open position as shown in FIG. 2A. During the sterilization process, the sterilant flows through the opening 164 between the main body 106 and the lid 108, and then through the second and third compartments 104B, 104C and into the first compartment 104A where it contacts and acts upon the test microorganisms 152 deposited on the biological indicator 150. After the sterilization process, the lid is moved downward into a closed position as shown in FIG. 2B. This results in the frangible ampoule 160 being broken. The liquid medium (e.g., viability detection medium) from the ampoule 160 then flows from the second compartment 104B into the first compartment 104A and contacts the test microorganisms 152. Gaseous reaction product generated as a result of the liquid medium coming into contact with viable test microorganism and/or with a chemical produced by viable test microorganism may flow from the first compartment 104A into the third compartment 104C, where it may come into contact with the sensing device 128. The sensing device 128 in the third compartment 104C may be used to detect the presence or absence of the gas.

Turning now to FIGS. 3-9, exemplary embodiments of the sensing device 128 and gas detection assembly 130 are shown.

Figure 3:
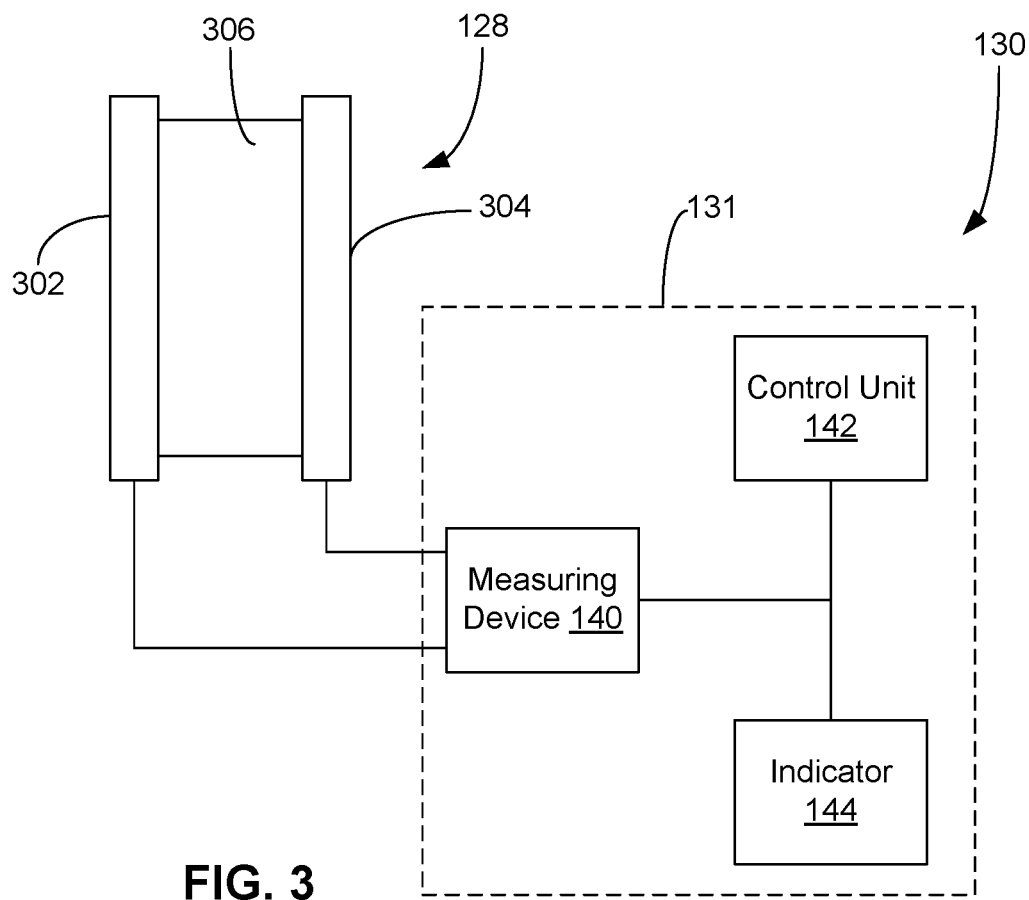
FIG. 3 is a schematic diagram of an exemplary detection assembly including a capacitive sensor.

In some embodiments, the sensing device 128 is a capacitive sensor. FIG. 3 schematically shows an exemplary embodiment of a gaseous reaction product detection assembly 130 including a capacitive sensor as the sensing device 128. In the example shown, the capacitive sensor is embodied as a parallel plate capacitor and includes a pair of electrical conductors 302, 304 (conducting plates) separated from one another. In the exemplary embodiment shown, the electrical conductors 302, 304 are separated by a dielectric material 306. In other embodiments, the electrical conductors 302, 304 are separated by an air gap and the air gap functions as the dielectric. It should also be appreciated that the capacitive sensor could be constructed in a different form, including, but not limited to, a cylindrical or spherical-shaped capacitor. If a spherical capacitor is used as the sensing device 128, one or more holes must be placed in the outer shell of the capacitor such that the gaseous reaction product can enter the capacitor.

The electrical conductors 302, 304 (conducting plates) may include aluminum, copper, silver, gold, platinum, indium tin oxide deposited on glass, or a combination of two or more thereof, or one or more other suitable conducting materials.

The dielectric material 306 is configured to absorb, adsorb, or otherwise interact or react with one or more components of the gaseous reaction product produced by the viable test microorganisms 152 of the biological indicator 150 being combined with the viability detection medium or one or more components of the gaseous reaction product produced by the combination of the chemical produced by the viable test microorganisms 152 of the biological indicator 150 and with the viability detection medium. As described above, in some embodiments, the gaseous reaction product may include methane carbon dioxide, nitrogen, hydrogen, hydrogen sulfide, ammonia, oxygen, and/or one or more volatile organic compounds. The dielectric material may absorb, adsorb, or otherwise interact or react with one or more of these components of the gaseous reaction product.

In some embodiments, the dielectric material includes a solid porous material through which the gaseous reaction product diffuses. Exemplary dielectric materials include porcelain (e.g., ceramic), mica, glass, cellulose, plastics (e.g., poly (ethylene terephthalate), poly (ethylene oxide), polyvinylidenefluoride, polyethylene, polypropylene, polyethylene-napthlate, polyphenylenesulfide, polycarbonate, polytetrafluoroethylene, polypropylene oxide, acrylic resin, polystyrene, poly(styrene-acrylonitrile), poly(acrylnitrile-butadiene-styrene), polyvinyl chloride, chlorinated polyether, poly(chlorotrifluoro ethylene), or a mixture of two or more thereof), and/or metal oxides (e.g., one or more transition metal oxides such as $TiO_2$, $V_2O_5$, $WO_3$, $SnO_2$, ZnO, CuO, AgO $Cr_2O_3$, $MnO_2$, $Fe_2O_3$, and the like and/or one or more non-transition metal oxides such as $Al_2O_3$, $Ga_2O_3$, SnO, $PbO_2$ and the like). It is also contemplated that metal oxides having mixed valency states, such as by way of example and not limitation, a metal oxide having a mixture of single and divalent oxide states may be used. In some embodiments, the volume of voids in the solid porous material divided by the total volume of the solid porous material may be in the range up to about 0.7, or from about 0.1 to about 0.7, or from about 0.3 to about 0.65.

In other embodiments, the dielectric material includes a fluid. As an example, the dielectric fluid may be a liquid having a dielectric constant in the range from 1 to about 90, or from about 5 to about 85, or from about 10 to about 80, measured at a temperature in the range from about −10° C. to about 60° C., or about 0° C. to about 50° C., or about 0° C. to about 40° C. The dielectric fluid may include water, one or more alcohols (e.g., methyl alcohol, ethyl alcohol, isopropyl alcohol), polyols (e.g., glycerol), aldehydes (e.g., acetaldehyde), ketones (e.g., acetone, methylethyl ketone), aromatic hydrocarbons (e.g., benzene, ethyl benzene), aliphatic hydrocarbons (e.g., propane, butane, pentane), fatty acids (e.g., stearic acid, oleic acid, lactic acid, linoleic acid), ethers (e.g., ethyl ether, diphenyl ether, ethylamyl ether, phenol ether), amines (e.g., dimethyl amine, diethyl amine, succinamide), esters (e.g., ethyl acetate), carboxylic acids and anhydrides (e.g., succinic acid, maleic anhydride), sugars (e.g., sucrose) natural oils (e.g., cotton seed oil, peanut oil), or a mixture of two or more thereof).

In other embodiments, the dielectric material is air.

As shown, the sensing device 128 is coupled to an electronic device, a measurement assembly 131, configured to measure a change in the capacitance of the capacitive sensor when the gaseous reaction product interacts with the dielectric material. The change in the capacitance indicates the presence of viable test microorganism of the biological indicator. The absence of a change in the capacitance indicates the absence of viable test microorganism of the biological indicator.

The measurement assembly 131 includes control unit 142, indicator 144, and measuring device 140. A power source (e.g., a battery), which is not shown, provides power to control unit 142, indicator 144 and measuring device 140. Control unit 142 may be a microprocessor or a microcontroller. Control unit 142 may also include (or is connected with) a data storage device for storing data. Indicator 144 may take the form of a visual and/or an audible indicator. These may include one or more LEDs, LCDs, speakers, and/or alarms. Indicator 144 may be used to provide a visual and/or audible indication of whether viable test microorganisms or spores are detected. For instance, a green LED may be illuminated to indicate the absence of viable test microorganisms (i.e., a successful sterilization cycle), while a red LED may be illuminated to indicate the presence of viable test microorganisms (i.e., an unsuccessful sterilization cycle). Alternatively, an audible alarm can be activated when it is determined that viable test microorganisms are present.

The sensing device may be sensitive enough to allow for detection of a small concentration of generated gaseous reaction product. In some examples, the capacitance of the sensing device may change with the presence of the gaseous reaction product at a concentration of 50 ppm or less. In some examples, the capacitance of the sensing device may change with the presence of the gaseous reaction product at a concentration of 100 ppm or less. In some examples, the capacitance of the sensing device may change with the presence of the gaseous reaction product at a concentration of 200 ppm or less. In some examples, the capacitance of the sensing device may change with the presence of the gaseous reaction product at a concentration of 500 ppm or less. The measuring device may detect the change in capacitance.

Figure 4:
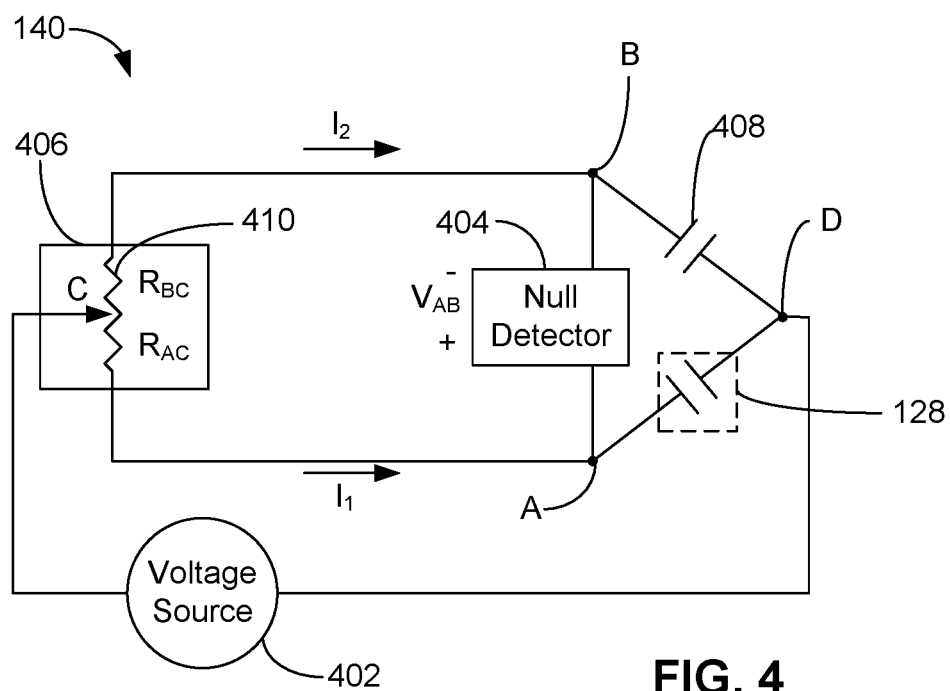
FIGS. 4-6 are schematic diagrams of exemplary measuring devices configured for use with a capacitive sensor.

With additional reference to FIG. 4, measuring device 140 may be in the form of a "bridge circuit." This bridge circuit includes a voltage source 402, a null detector 404, an electronic potentiometer 406, and a capacitor 408 of a known capacitance $C_1$. The capacitive sensor 128 is also connected in the circuit. Capacitance ($C_X$) of the capacitive sensor 128 will vary in response to the gaseous reaction product produced by the viable test microorganisms 152 of the biological indicator 150 combined with the viability detection medium or the gaseous reaction product produced by the combination of the chemical produced by the viable test microorganisms 152 of the biological indicator 150 and with the viability detection medium.

Electronic potentiometer 406 functions in the same manner as a mechanical potentiometer. In this regard, electronic potentiometer 406 is a three terminal device. Between two of the terminals is a resistive element 410. The third terminal known as the "wiper" is connected to various points along the resistive element. In the illustrated embodiment, the wiper is digitally controlled by control unit 142. The wiper divides the resistive element 410 into two resistors $R_{BC}$ and $R_{AC}$. Electronic potentiometer 406 may take the form of a digitally programmable potentiometer (DPP™) available from Catalyst Semiconductor, Inc. of Sunnyvale, Calif.

In one embodiment, voltage source 402 provides an AC voltage signal, such as a sinusoidal or pulse waveform. Null detector 404 is a device for detecting a null condition (i.e., a short circuit), such as a galvanometer, a voltmeter, a frequency-selective amplifier, and the like.

The elements of the bridge circuit are connected between junctions AC, BC, AD, and BD. Electronic potentiometer 406 is operated by control unit 142 to vary the resistances $R_{BC}$ and $R_{AC}$ until the potential difference between junctions A and B ($V_{AB}$) is zero. When this situation exists, the bridge is said to be balanced or is "nulled." The following relationships then hold for voltages in the main branches:

$$V_{AC} = V_{BC}, \text{ and } V_{AD} = V_{BD},$$

where $V_{AC}$ is the voltage between junctions A and C, $V_{BC}$ is the voltage between junctions B and C, $V_{AD}$ is the voltage between junctions A and D, and $V_{BD}$ is the voltage between junctions B and D. Accordingly, $$V_{AD}/V_{AC} = V_{BD}/V_{BC}$$

$$V_{AD} = V_{BD}/(V_{AC}/V_{BC})$$

The capacitive sensor 128 is connected between junctions A and D, and capacitor 408 of known capacitance $C_1$ is connected between junctions B and D. Electronic potentiometer 406, connected from junction A to junction C to junction B, is adjusted by control unit 142 to vary the voltages $V_{AC}$ and $V_{BC}$.

When a null is detected by the null detector 404, current $I_1$ flows from junction C to junction A to junction D, and a current $I_2$ flows from junction C to junction B to junction D. The voltage $V_{AC}$ across junctions A to C, and the voltage $V_{BC}$ across junctions B to C are:

$$V_{AC} = I_1 R_{AC} \text{ and } V_{BC} = I_2 R_{BC}.$$

The voltage across a capacitor with capacitance C, current I, and frequency f is:

$$V = \frac{I}{2\pi f C}$$

Therefore, the voltages $V_{AD}$ and $V_{BD}$ may be expressed as:

$$V_{AD} = \frac{I_1}{2\pi f C_x} \quad V_{BD} = \frac{I_2}{2\pi f C_1}$$

As discussed above, $V_{AD} = V_{BD}/(V_{AC}/V_{BC})$, $V_{AC} = I_1 R_{AC}$, and $V_{BC} = I_2 R_{BC}$. Therefore, $$C_x = C_1 \left( \frac{R_{BC}}{R_{AC}} \right).$$

In view of the forgoing relationship, when a null condition is detected, the resistance values for $R_{BC}$ and $R_{AC}$, along with the known capacitance $C_1$ of capacitor 315, can be used to determine the value of capacitance $C_x$ of the capacitive sensor 128.

By configuring capacitive sensor 128 as an element within the bridge circuit, a measure of resistance values $R_{AC}$ and $R_{BC}$, when the bridge is balanced or nulled, can be used to determine the capacitance $C_x$ of the capacitive sensor 128. Changes to this capacitance $C_x$ of the capacitive sensor 128 is indicative of the presence of viable test microorganisms of the biological indicator.

Figure 5:
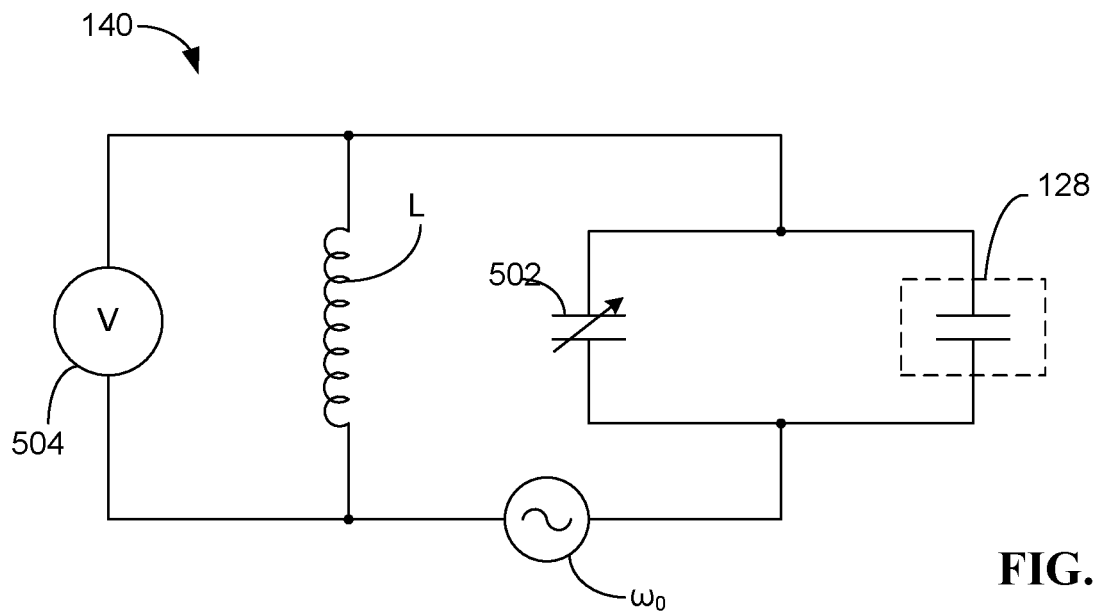

While measuring device 140 is shown in FIG. 4 as being in the form of a bridge circuit, other types of circuits and techniques (including other types of bridge circuits, and capacitance meters) may be used to measure capacitance. For example, FIG. 5 illustrates an alternative measuring device 140. Measuring device 140 in FIG. 5 is an LC resonant circuit, including a variable capacitor 502 (having a capacitance $C_A$). The capacitive sensor 128 (having a capacitance $C_x$) is also coupled in the circuitry. Since the resonance frequency $\omega_0 = [L(C_A + C_x)]^{-1/2}$, the capacitance $C_x$ of capacitive sensor 128 can be determined. Changes to the capacitance $C_x$ of capacitive sensor 128 is indicative of the presence of viable test microorganisms of the biological indicator.

Figure 6:
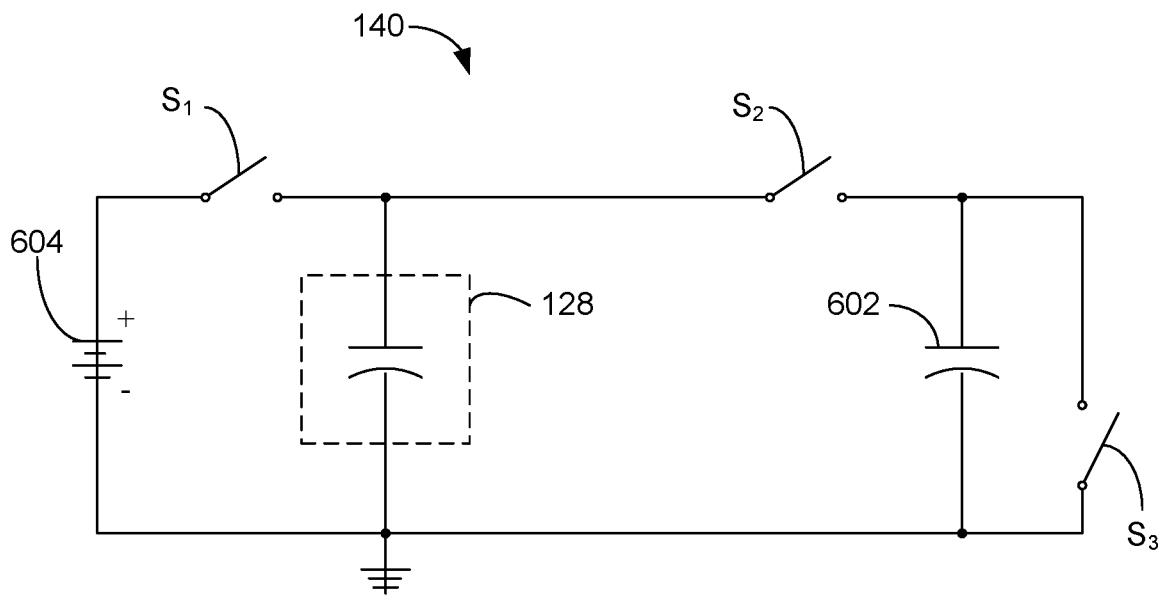

FIG. 6 illustrates yet another alternative measuring device 140 suitable for use in connection with the capacitive sensor 128. Measuring device 140 in FIG. 6 is a "charge transfer" sensor circuit. Charge transfer sensor circuits are recognized to provide resolutions of fractions of a femtoFarad. In a charge transfer sensor circuit the capacitance $C_x$ of a capacitive sensor 128 is determined by charging the sensing electrode to a fixed potential, and then transferring that charge to a charge detector including a capacitor 602 of known capacitance $C_s$. Capacitive sensor 128 having unknown capacitance $C_x$ acts as a sensing element, as described above. Capacitive sensor 128 is first connected to a DC reference voltage 504 ($V_r$) via a switch $S_1$. Switch $S_1$ is reopened after capacitive sensor 128 is satisfactorily charged to the potential of $V_r$. Then, after as brief as possible a delay so as to minimize leakage effects caused by conductance, switch $S_2$ is closed and the charge (Q) present on capacitive sensor 128 is transferred to capacitor 602 (i.e., the charge detector). Once the charge Q is satisfactorily transferred to capacitor 602, switch $S_2$ is reopened. By reading voltage $V_s$, the capacitance $C_x$ of capacitive sensor 128 can be determined. $V_s$ may be input to an amplifier to provide the scaling necessary to present an analog-to-digital converter (ADC) with a useful range of voltage for digital processing. Switch $S_3$ acts as a reset means to reset the charge between charge transfer cycles, so that each charge transfer cycle has a consistent initial condition. Switches $S_1$, $S_2$ and $S_3$ may be electromechanical switches or transistors. Digital control logic may be used to control switches $S_1$, $S_2$ and $S_3$. Capacitor 602 may be significantly larger than capacitive sensor 128.

The equations governing the measuring device 140 shown in FIG. 6 are as follows:

$$V_s = V_r[C_x/(C_x + C_s)], \text{ therefore}$$

$$C_x = V_s C_s/[V_r - V_s].$$

The charge-transfer sensor has been applied in a self-contained capacitance-to-digital-converter (CDC) integrated circuit (IC). For example, Quantum Research Group produces a QProx™ CDC sensor IC (e.g., QT300 and QT301 CDC sensor ICs) for detecting femtofarad level changes in capacitance. The CDC sensor IC outputs a digital value corresponding to the detected input capacitance. The value of an external sampling capacitor controls the gain of the sensor.

Other high sensitivity circuitry is provided by such devices that may be used include the PTL 110 capacitance transducer from Process Tomography Limited of Cheshire, United Kingdom. The PTL 110 measures small values of capacitance (up to 10 pF) with a resolution of 1 fF. A 7600 Plus Precision LCR Meter Capacitance Bridge from IET Labs, Inc. of Westbury, N.Y., allows for measurement of capacitances in the range from 0.01 fF to 10 F. Tektronix produces the Tektronix 130 LC Meter that measures capacitance from 0.3 pF to 3 pF. It has also been acknowledged in the prior art literature that capacitance sensor circuits using modern operational amplifiers and analog-to-digital converters (ADCs) can easily obtain resolutions to 0.01 pF. In an embodiment, a dielectric cell may be used to provide a more accurate capacitance reading by screening out extraneous electrical signals; see, ASTM D150.

Figure 7A:
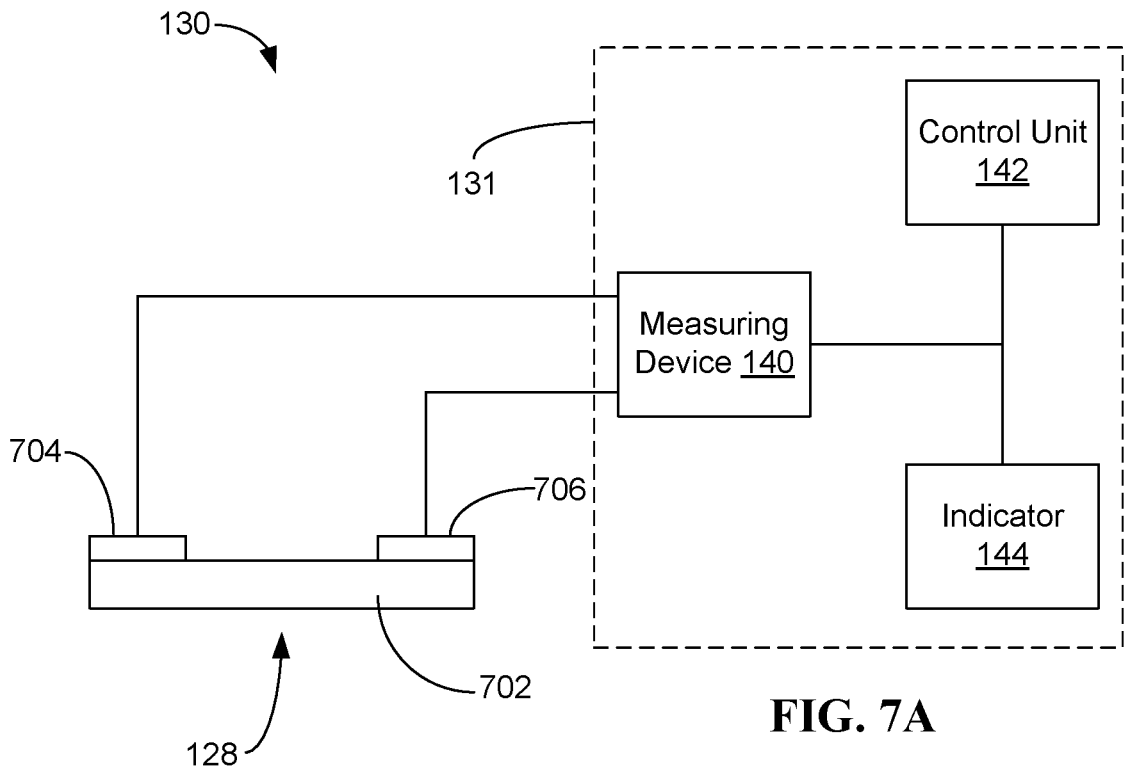
FIGS. 7A and 7B are schematic diagrams of an exemplary detection assembly including a resistive sensor.

In some embodiments, the sensing device 128 is a resistive sensor. FIG. 7A schematically shows an exemplary embodiment of a gas detection assembly 130 including a resistive sensor as the sensing device 128. In the example shown, the resistive sensor includes a substrate 702 and a plurality of electrodes (e.g., working electrode 704 and reference electrode 706) provided on the substrate 702. In some embodiments, the electrodes 704,706 are coupled to one another by only the substrate 702. Accordingly, the substrate 702 may be configured to absorb, adsorb, or otherwise interact or react with one or more components of the gaseous reaction product, the presence of the gaseous reaction product changing (increasing or decreasing) the electrical conductivity of the substrate. The substrate 702 may be a porous material through which the gaseous reaction product diffuses. In some embodiments, the volume of voids in the porous solid divided by the total volume of the porous solid may be in the range up to about 0.7, or from about 0.1 to about 0.7, or from about 0.3 to about 0.65.

Figure 7B:
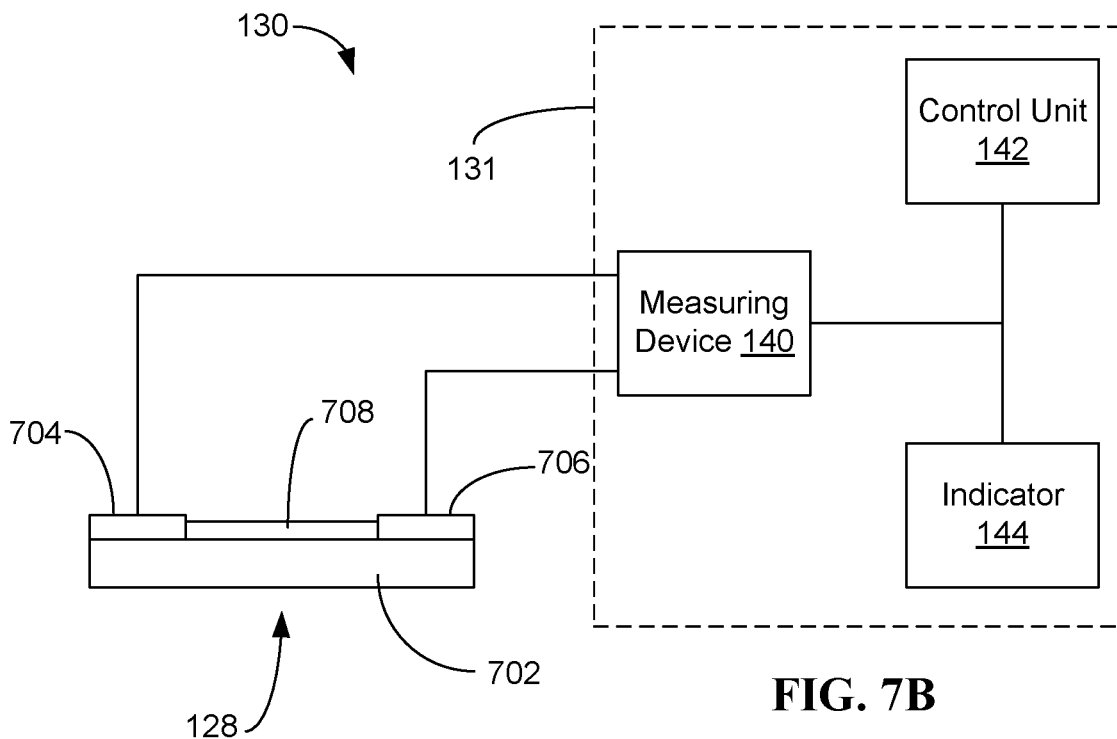
Figure 8:
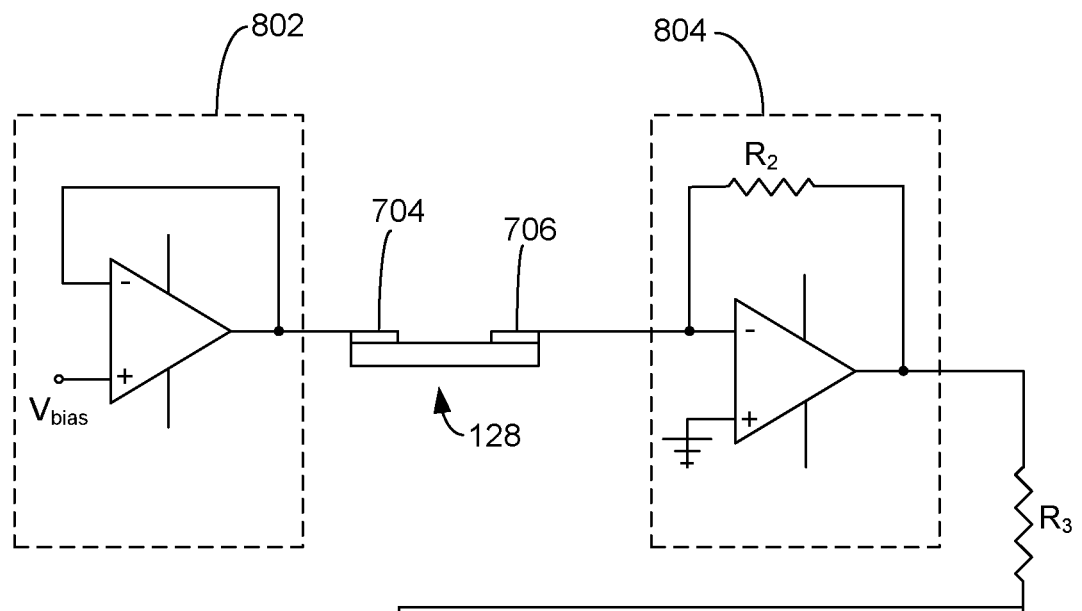
FIG. 8 is a schematic diagram of an exemplary measuring device configured for use with a resistive sensor.
Figure 8:
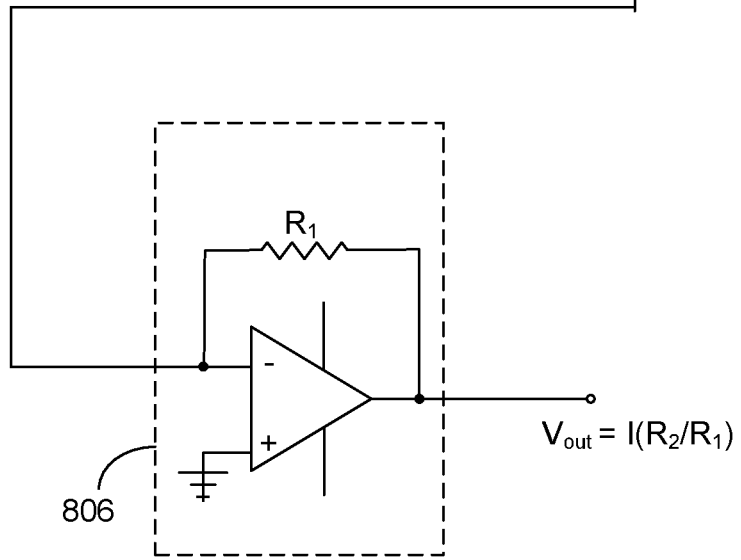

In other embodiments, the electrodes 704,706 are coupled to one another by one or more additional layers (see FIG. 7B). The one or more additional layers 708 may bridge between the electrodes 704,706. In some examples, the one or more additional layers 708 may be provided on the substrate 702. The one or more additional layers 708 may be conductive or semi-conductive layers that are configured to absorb, adsorb, or otherwise interact or react with the gaseous reaction product, the presence of the gaseous reaction product changing (increasing or decreasing) the electrical conductivity of the one or more layers.

As described above, in some embodiments, the gaseous reaction product may include methane carbon dioxide, nitrogen, hydrogen, hydrogen sulfide, ammonia, oxygen, and/or one or more volatile organic compounds. The substrate 702 and/or the one or more additional layers 708 may absorb, adsorb, or otherwise interact or react with one or more of these components of the gaseous reaction product.

In some embodiments, the substrate 702 may be an insulator or a semi-conductor prior to being contacted by the gaseous reaction product. In an embodiment, at least a portion of the substrate 702 may be amorphous. For example, from about 5 to about 30% by volume of the substrate may be amorphous, or from about 10 to about 25% by volume may be amorphous. In an embodiment, at least a portion of the substrate 702 may be crystalline. The substrate 702 may contain one or more amorphous layers in contact with one or more crystalline layers.

In some examples, the substrate 702 may include poly (ethylene terephthalate), poly (ethylene oxide), polyvinylidenefluoride, polyethylene, polypropylene, polyethylene-napthlate, polyphenylenesulfide, polycarbonate, polytetrafluoroethylene, polypropylene oxide, acrylic resin, polystyrene, poly(styrene-acrylonitrile), poly(acrylnitrile-butadiene-styrene), polyvinyl chloride, chlorinated polyether, poly(chlorotrifluoro ethylene), or a mixture of two or more thereof. The substrate 702 may include glass and/or ceramic. The substrate 702 may include carbon and/or graphite. In some embodiments, the substrate 702 may include one or more metals, metal meshes, metal screens, and/or nanomaterials.

In some embodiments, the substrate 702 may be a conductive material.

In some examples, the substrate 702 may include a solid polymer electrolyte material. The solid polymer electrolyte may include a salt dispersed within a solid polymer to provide ionic conductivity to the electrolyte. Examples of polymers include poly(oxides), poly(vinyl ethers), polyvinylpyrrolidone, poly(acrylics) and poly(methacrylics). Examples of poly(acrylics) and poly(methacrylics) include, but are not limited to, poly(acrylic acid), poly(ethyl acrylate), poly(3-ethoxyethylacrylate), poly(4-cyanophenyl acrylate), poly(2-cyanoethyl acrylate), poly(4-methoxyphenyl acrylate) and poly(n-pentyl acrylate).

The substrate 702 may include any of the above-indicated polymers and one or more fillers. The fillers may be electrically conductive or non-conductive. The fillers may be inorganic, organic, or a mixture thereof. The inorganic fillers may include one or more silicates, oxides, carbonates, sulfates, hydroxides, carbons, metals, glass, mixtures of two or more, and the like. Examples of the fillers that may be used include clay, talc, mica, asbestos, feldspar, bentonite clay, wollastonite, fuller's earth, pumice, pyrophillite, rottenstone, slate flour, vermiculite, calcium silicate (precipitated), magnesium silicate (precipitated), aluminum oxide, hydrated alumina, antimony trioxide, magnesium oxide, titanium dioxide, zinc oxide, silica, quartz, diatomaceous earth, tripoli, pyrogenic, hydrogel, aerogel, calcium carbonate (precipitated), ground limestone, ground marble, barium carbonate (precipitated), magnesium carbonate (precipitated), barium sulfate, barytes, blanc fixe, calcium sulfate, calcium hydroxide, magnesium hydroxide, carbon black, furnace black, lampblack, acetylene, graphite, carbon fibers, metal powders (e.g., copper, aluminum, bronze, lead, zinc, steel), metal fibers, metal whiskers, metal wire, barium ferrite, magnetite, molybdenum disulfide, glass fibers, glass flakes, ground glass, mixtures of two or more thereof, and the like.

In some embodiments, the one or more additional layers 708 may include one or more conductive polymers. In some embodiments, the one or more additional layers 708 may include one or more semi-conductor materials. The materials of the one or more additional layers 708 may be similar to the materials described above in connection with the substrate. The material of the one or more additional layers 708 may have an affinity for one or more components of the gaseous reaction product, and/or the one or more additional layers may absorb, adsorb, or otherwise interact or react with one or more components of the gaseous reaction product, the presence of the gaseous reaction product changing (increasing or decreasing) the electrical conductivity of the one or more additional layers.

The substrate 702 and/or the one or more additional layers 708 may in some embodiments include a dopant that is configured to react with the gaseous reaction product. This reaction may lower the dopant concentration in the substrate, changing (e.g., increasing or lowering) the electrical conductivity of the substrate and/or the one or more additional layers.

The electrodes 704,706 may include aluminum, copper, silver, gold, platinum, indium tin oxide deposited on glass, or a combination of two or more thereof, or one or more other suitable conducting materials.

As shown, the sensing device 128 is coupled to an electronic device, a measurement assembly 131, configured to measure a change in the resistance of the resistive sensor 128 when the gaseous reaction product interacts with the substrate and/or one or more additional conductive layers. The change in the resistance indicates the presence of viable test microorganism of the biological indicator. The absence of a change in the resistance indicates the absence of viable test microorganism of the biological indicator.

The measurement assembly 131 includes control unit 142, indicator 144, and measuring device 140. A power source (e.g., a battery), which is not shown, provides power to control unit 142, indicator 144 and measuring device 140. Control unit 142 may be a microprocessor or a microcontroller. Control unit 142 may also include (or is connected with) a data storage device for storing data. Indicator 144 may take the form of a visual and/or an audible indicator. These may include one or more LEDs, LCDs, speakers, and/or alarms. Indicator 144 may be used to provide a visual and/or audible indication of whether viable test microorganisms or spores are detected. For instance, a green LED may be illuminated to indicate the absence of viable test microorganisms (i.e., a successful sterilization cycle), while a red LED may be illuminated to indicate the presence of viable test microorganisms (i.e., an unsuccessful sterilization cycle). Alternatively, an audible alarm can be activated when it is determined that viable test microorganisms are present.

The sensing device may be sensitive enough to allow for detection of a small concentration of generated gaseous reaction product. In some examples, the current passing through the sensing device may change with the presence of the gaseous reaction product at a concentration of 50 ppm or less. In some examples, the current passing through the sensing device may change with the presence of the gaseous reaction product at a concentration of 100 ppm or less. In some examples, the current passing through the sensing device may change with the presence of the gaseous reaction product at a concentration of 200 ppm or less. In some examples, the current passing through the sensing device may change with the presence of the gaseous reaction product at a concentration of 500 ppm or less. The measuring device may detect the change in current. With additional reference to FIG. 8, measuring device 140 may be in the form of a potentiostat. The circuitry includes potential control unit 802, current follower 804, and current amplifier 806. Potential control unit 802 may be provided to maintain a stable voltage potential at the working electrode 704 with respect to the reference electrode 706. Control unit 142 may control the potential control unit 802. Current follower 804 may be provided to convert the current from sensor 128 to a voltage and to process further signal processing. Current amplifier 804 may be provided to enable measuring of low-level currents of the nA and pA ranges. Changes to the current of resistive sensor 128 is indicative of the presence of viable test microorganisms of the biological indicator.

Figure 9:
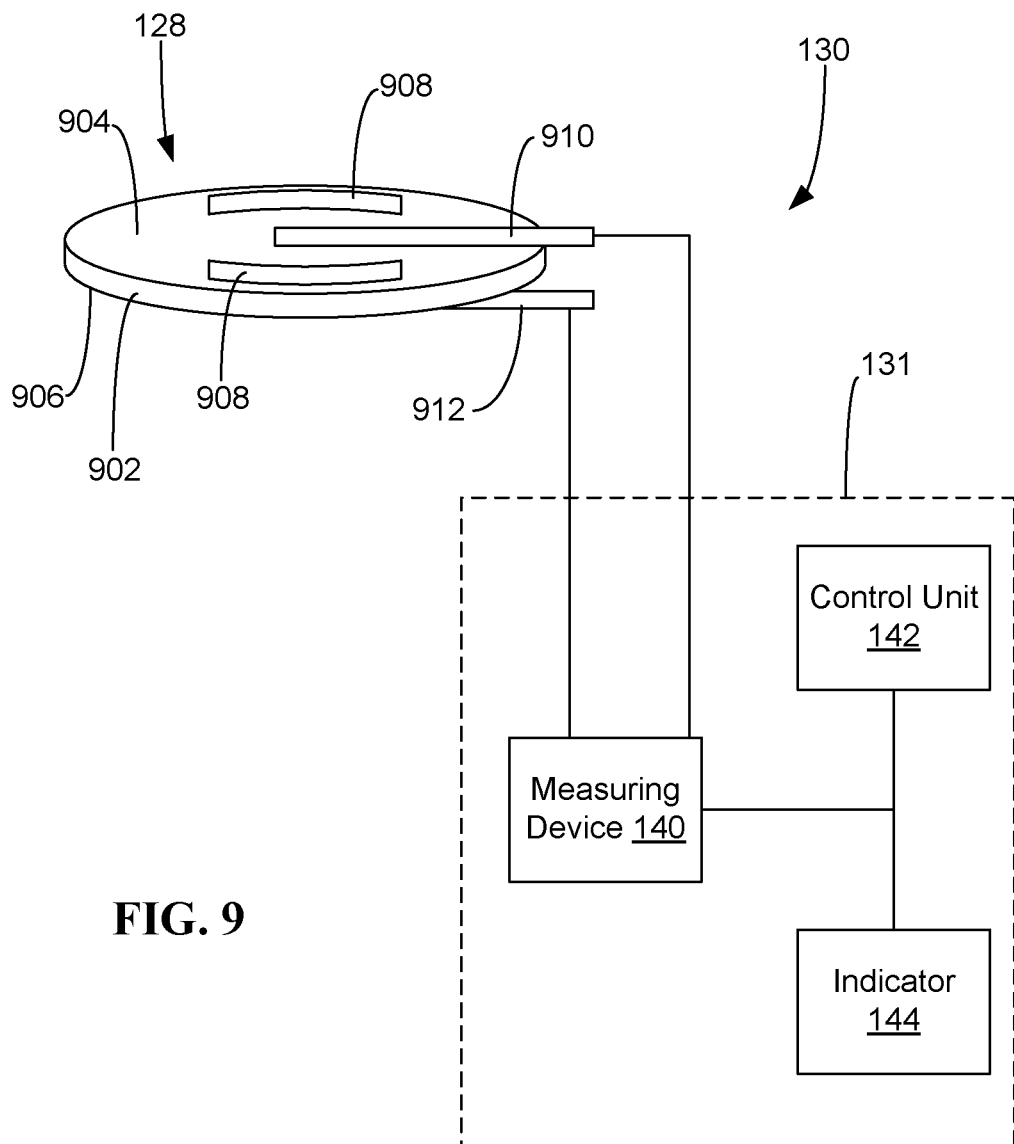
FIG. 9 is a schematic diagram of an exemplary detection assembly including an electro-mechanical sensor.

In some embodiments, the sensing device 128 is an electro-mechanical sensor. FIG. 9 schematically shows an exemplary embodiment of a gas detection assembly 130 including an electro-mechanical sensor as the sensing device 128. In the example shown, the electro-mechanical sensor includes a substrate 902 having a first major surface 904 and a second major surface 906 opposite the first major surface 904. A layer or coating of a material 908 is present at at least one of the major surfaces 904, 906. The layer/coating of material 908 may absorb, adsorb, or otherwise interact with or react with one or more components of the gaseous reaction product produced by the viable test microorganisms 152 of the biological indicator 150 combined with the viability detection medium or the gaseous reaction product produced by the combination of the chemical produced by the viable test microorganisms 152 of the biological indicator 150 and the viability detection medium. A change in the oscillation frequency of the electromechanical sensor due to interaction/reaction of the gaseous reaction product with the layer/coating of material indicates the presence of viable test microorganism of the biological indicator.

As described above, in some embodiments, the gaseous reaction product may include methane, carbon dioxide, nitrogen, hydrogen, hydrogen sulfide, ammonia oxygen, and/or one or more volatile organic compounds. The layer/coating of material 908 may absorb, adsorb, or otherwise interact or react with one or more of these components of the gaseous reaction product.

The substrate may be a moving or suspended component. In some embodiments, substrate 902 is a piezoelectric device, and more preferably, is a quartz crystal (e.g., a quartz crystal microbalance). Other piezoelectric materials, such as by way of example and not limitation, Rochelle salt, barium titanate, tourmaline, polyvinylidene fluoride and crystals that lack a center of symmetry are also contemplated. In the embodiment shown, the substrate 902 is a flat, circular quartz disk having a first planar, major surface 904 and a second planar, major surface 906.

An electrode 910 is disposed on the first major surface 904 and an electrode 912 is disposed on the second major surface 906. The electrodes 910, 912 may be formed of any suitable electrically conductive material. Exemplary materials include aluminum, copper, silver, gold, platinum, or a combination of two or more thereof. Electrical leads are attached to the electrodes.

At least one of the two major surfaces 904, 906 of the substrate 902 is coated with a layer of a material 908 that interacts with (e.g., adsorbs or absorbs), or is reactive with, the gaseous reaction product produced by the viable test microorganisms 152 of the biological indicator 150 combined with the viability detection medium or the gaseous reaction product produced by the combination of the chemical produced by the viable test microorganisms 152 of the biological indicator 150 and the viability detection medium. In the embodiment shown, the layer/coating 908 is defined by two arcuate or crescent-shaped layer areas of material applied to first major surface 904 of the substrate 902. The arcuate layer areas are disposed on first major surface 904 such that electrode 910 is disposed therebetween. The material forming the coating is preferably fixedly attached to the surface of the substrate. In other embodiments, both of the major surfaces 904, 906 of the substrate 902 are coated with the material.

The material that forms the layer/coating 908 may be any suitable material that interacts with, or is reactive with, the gaseous reaction product generated by the viable test microorganisms of the biological indicator. In some embodiments, the coating may include one or more inorganic materials. In some embodiments, the coating may include one or more organic materials. In some embodiments, the coating may include one or more metal oxides. Exemplary metal oxides include one or more transition metal oxides such as $TiO_2$, $V_2O_5$, $WO_3$, $SnO_2$, ZnO, CuO, AgO $Cr_2O_3$, $MnO_2$, $Fe_2O_3$, and the like and/or one or more non-transition metal oxides such as $Al_2O_3$, $Ga_2O_3$, SnO, $PbO_2$ and the like. It is also contemplated that metal oxides having mixed valency states, such as by way of example and not limitation, a metal oxide having a mixture of single and divalent oxide states may be used. In some embodiments, the coating may include one or more polymers (e.g., poly (ethylene terephthalate), poly (ethylene oxide), polyvinylidenefluoride, polyethylene, polypropylene, polyethylene-napthlate, polyphenylenesulfide, polycarbonate, polytetrafluoroethylene, polypropylene oxide, acrylic resin, polystyrene, poly(styrene-acrylonitrile), poly(acrylnitrile-butadiene-styrene), polyvinyl chloride, chlorinated polyether, poly(chlorotrifluoro ethylene), or a mixture of two or more thereof).

In some embodiments, the coating may include an additive to increase attraction to the gaseous reaction product or catalyze the gas.

The coating may be formed by a thin film deposition process. It should be understood that the term "thin film deposition" is inclusive of Physical Vapor Deposition (PVD) and Chemical Vapor Deposition (CVD). PVD includes the processes of evaporation, ion-beam assisted electron beam deposition, and "sputtering" (which includes ion beam deposition).

Evaporation includes processes such as electron beam evaporation (also referred to herein as "electron beam deposition"), as well as processes wherein a material is heated inside a vacuum chamber by a heater to form a vapor, without use of an electron beam. The heating is classified as (a) resistive or (b) inductive. The evaporation processes which do not use an electron beam are commonly used to deposit $SiO_2$ or SiO thin films, and can also be used in conjunction with an ion-beam assist. Ion-beam assisted evaporation (with and without use of an e-beam) are collectively referred to herein as "ion-bean assisted deposition."

Sputtering refers to a glow discharge process whereby bombardment of a cathode releases atoms from the surface which then deposit onto a nearby surface to form a coating. For example, sputtering occurs when energetic ionized particles impinge on the surface of a target material, causing the emission of particles and erosion of the surface of a solid. This particular sputtering process is also referred to herein as "ion beam deposition."

In some embodiments, the layer/coating 908 may be porous, with the volume of voids in the porous layer/coating divided by the total volume of the porous layer/coating being in the range up to about 0.7, or from about 0.1 to about 0.7, or from about 0.3 to about 0.65.

As shown, the sensing device 128 is coupled to an electronic device, a measurement assembly 131, configured to measure a change in the oscillation frequency of the electromechanical sensor when the gaseous reaction product interacts with the material. The change in the oscillation frequency of the electromechanical sensor indicates the presence of viable test microorganism of the biological indicator. The absence of a change in the oscillation frequency of the electromechanical sensor indicates the absence of viable test microorganism of the biological indicator.

The measurement assembly 131 includes control unit 142, indicator 144, and measuring device 140. A power source (e.g., a battery), which is not shown, provides power to control unit 142, indicator 144 and measuring device 140. Control unit 142 may be a microprocessor or a microcontroller. Control unit 142 may also include (or be connected with) a data storage device for storing data. Indicator 144 may take the form of a visual and/or an audible indicator. These may include one or more LEDs, LCDs, speakers, and/or alarms. Indicator 144 may be used to provide a visual and/or audible indication of whether viable test microorganisms or spores are detected. For instance, a green LED may be illuminated to indicate the absence of viable test microorganisms (i.e., a successful sterilization cycle), while a red LED may be illuminated to indicate the presence of viable test microorganisms (i.e., an unsuccessful sterilization cycle). Alternatively, an audible alarm can be activated when it is determined that viable test microorganisms are present.

Figure 10:
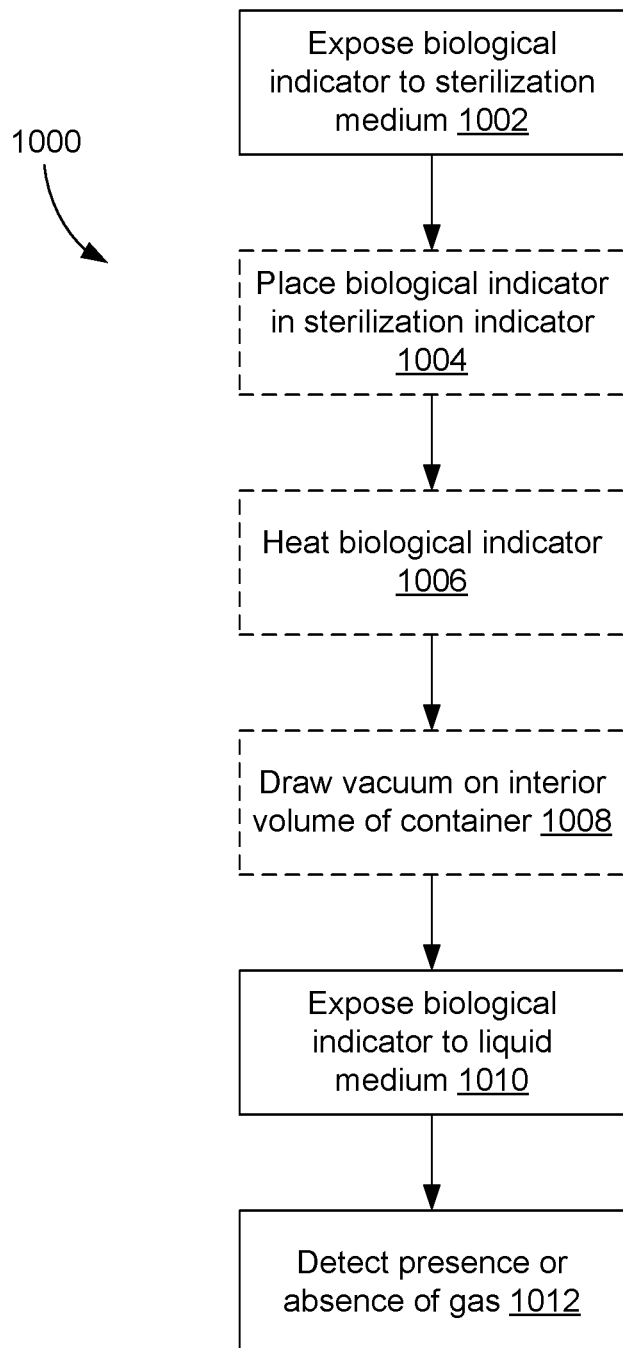
FIG. 10 is a flow chart of an exemplary process for determining the viability of a biological indicator.

The sensing device may be sensitive enough to allow for detection of a small concentration of generated gaseous reaction product. In some examples, the sensing device may change in oscillation frequency with the presence of the gaseous reaction product at a concentration of 50 ppm or less. In some examples, the sensing device may change in oscillation frequency with the presence of the gaseous reaction product at a concentration of 100 ppm or less. In some examples, the sensing device may change in oscillation frequency with the presence of the gaseous reaction product at a concentration of 200 ppm or less. In some examples, the sensing device may change in oscillation frequency with the presence of the gaseous reaction product at a concentration of 500 ppm or less. The measuring device may detect the change in oscillation frequency. The measuring device 140 includes an oscillating circuit (not shown) that is connected to the electro-mechanical sensor 128 to convert movement of sensor into electrical signals, as is conventionally known. In an example, the natural frequency of a piezoelectric material (such as quartz crystal) with the coating thereon is measured. Upon exposure to the gaseous reaction product generated by the viable test microorganisms of the biological indicator, the frequency will change in relation to a change in mass of a layer on the device, as a result of exposure of the coating to the gas. Specifically, the frequency of a piezoelectric device is related to the mass change, as determined by the Sauerbre equation:

$$\Delta f = -(C_f)(\Delta m)$$

$$\Delta f = -(f_o^2/N\rho)\Delta m$$

where $\Delta f$ is the frequency change; $\Delta m$ is the mass change per unit area on the surface of the piezoelectric device; $C_f$ is a sensitivity constant; $f_o$ is the operating frequency of the piezoelectric device prior to the mass change; N is the frequency constant for the piezoelectric device; and $\rho$ is the density of the piezoelectric device, Turning now to FIG. 10, an exemplary process for determining the viability of a biological indicator is shown at 1000. At step 1002, the biological indicator is exposed to a sterilization medium. Exposure to a sterilization medium may occur as part of a sterilization process. The sterilization process may employ any suitable sterilant (sterilization medium). Exemplary sterilization media include steam, dry heat, radiation, plasma, ozone, vaporized hydrogen peroxide, vaporized peracetic acid, ethylene oxide, chlorine dioxide, one or more gaseous sterilants, and/or one or more liquid sterilants. The sterilant gas may be mixed with a carrier gas. The carrier gas may include air, nitrogen, and the like. The sterilization process may be conducted for an effective period of time to achieve at least a 4 log reduction, or at least a 5 log reduction, or at least a 6 log reduction in the number of test microorganisms, bacteria or spores capable of reproduction, metabolism and/or growth. When at least a 6 log reduction is achieved, the process may be referred to as a sterilization process. When a 4 log reduction or a 5 log reduction is achieved, the process may be considered to be less rigorous than a sterilization process, but nevertheless useful for various disinfection, sanitization, decontamination and/or cleaning applications.

In some embodiments, the biological indicator is added to the sterilization detection device subsequent to being exposed to the sterilization medium. As an example, and with exemplary reference to FIG. 1, the biological indicator that has been subjected to the sterilization process may be placed in the interior volume of the container. Accordingly, optionally at step 1004, the biological indicator is placed in the sterilization detection device. In other embodiments, and with exemplary reference to FIG. 2 and the description set forth above, the biological indicator is added to the container prior to being exposed to the sterilization medium. Accordingly, in such embodiments, step 1004 may be omitted.

In some embodiments, the biological indicator is heated subsequent to the step of exposing the biological indicator to a sterilization medium and prior to the step of exposing the biological indicator to the viability detection medium. Accordingly, optionally at step 1006, the biological indicator is heated. In an example, the biological indicator is heated within the range of 20° C.-100° C. In another example, the biological indicator is heated within the range of 20° C.-70° C. In another example, the biological indicator is heated within the range of 30° C.-50° C. In another example, the biological indicator is heated within the range of 50° C.-70° C. In another example, the biological indicator is heated within the range of 70° C.-90° C. In other embodiments, no such heating is conducted. Accordingly, in some embodiments, step 1006 may be omitted.

In some embodiments, detection the presence or absence of gaseous reaction product produced by the viable test microorganisms 152 of the biological indicator 150 combined with the viability detection medium or the gaseous reaction product produced by the combination of the chemical produced by the viable test microorganisms 152 of the biological indicator 150 and the viability detection medium is conducted under vacuum. Accordingly, optionally at step 1008, a vacuum (e.g., a partial vacuum) is drawn on the interior volume 104 of the container 102. In some implementations, at step 1008, a predetermined amount of gas (e.g., oxygen) may be introduced into the interior volume of the container (e.g., via port 125). The gas may be provided in an amount such that partial vacuum is provided in the interior volume, but oxygen may be present for growth of the test microorganisms. In other embodiments, no vacuum is applied. Accordingly, in some embodiments, step 1008 may be omitted.

At step 1010, the biological indicator is exposed to the viability detection medium. As described above, in some embodiments, the viability detection medium includes a nutrient containing assay medium that causes viable test microorganisms of the biological indicator to produce a gaseous reaction product including one or more components (e.g., carbon dioxide, oxygen, nitrogen, hydrogen, hydrogen sulfide, ammonia, methane, and/or one or more volatile organic compounds). In some embodiments, a viability detection medium (e.g., hydrogen peroxide) is provided that, when combined with viable test microorganisms of the biological indicator or with a chemical produced by viable test microorganisms of the biological indicator, produces a gaseous reaction product (e.g., oxygen). In the example shown in FIG. 1, a predetermined amount of the liquid medium 120 is dispensed from the liquid dispenser 110. In the example shown in FIG. 2, the ampoule 160 may be broken, releasing the predetermined amount of liquid medium 120. The amount of liquid medium that is released may be any suitable amount, and may depend on one or more factors such as the size of the biological indicator. In one examples, the amount of liquid medium may be 20 µl-500 µl. In other examples, the amount of liquid medium may be 500 µl-5.0 ml.

At step 1012, the presence or absence of a gaseous reaction product produced by the viable test microorganisms 152 of the biological indicator 150 combined with the viability detection medium or a gaseous reaction product produced by the combination of the chemical produced by the viable test microorganisms 152 of the biological indicator 150 and the viability detection medium is detected. The presence or absence of this gaseous reaction product is detected using a sensing device. As described above, the sensing device may include a capacitive sensor, an electro-mechanical sensor, and/or a resistive sensor. The presence of the gaseous reaction product indicates the presence of viable test microorganisms and the absence of the gaseous reaction product indicates the absence of viable test microorganisms.

In the case of a capacitive sensor, a change in the capacitance of the capacitive sensor as detected by the gaseous reaction product detection assembly indicates the presence of viable test microorganism of the biological indicator; and the absence of a change in the capacitance of the capacitive sensor as detected by the gaseous reaction product detection assembly indicates the absence of viable test microorganism of the biological indicator. In the case of a resistive sensor, a change in the resistance indicates the presence of viable test microorganism of the biological indicator; and the absence of a change in the resistance indicates the absence of viable test microorganism of the biological indicator. In the case of an electro-mechanical sensor, a change in the oscillation frequency of the electro-mechanical sensor indicates the presence of viable test microorganism of the biological indicator; and the absence of a change in the oscillation frequency of the electromechanical sensor indicates the absence of viable test microorganism of the biological indicator.

The production of gaseous reaction product by the viable test microorganisms 152 of the biological indicator 150 combined with the liquid medium or the gaseous reaction product produced by the combination of the chemical produced by the viable test microorganisms 152 of the biological indicator 150 and the liquid medium may occur instantaneously or within a short amount of time after the liquid medium is brought into contact with the biological indicator. Furthermore, the sensitivity of the sensing device may allow for detection of a small amount of gaseous reaction product. As such, it is possible to obtain an instantaneous or rapid read on whether a sterilization process has been successful by measuring a change in the capacitance/current/oscillation frequency of the sensing device. The determination of whether live test microorganisms or spores are present, can be accomplished instantaneously, or within a period of time of up to about 2,000 seconds, or up to about 1500 seconds, or up to about 1000 seconds, or up to about 500 seconds, or up to about 200 seconds, or up to about 100 seconds, or up to about 50 seconds, or up to about 30 seconds, or in the range from about 5 to about 2000 seconds, or from about 10 to about 1800 seconds, or from about 20 to about 1500 seconds, or from about 30 to about 1200 seconds, or from about 50 to about 1000 seconds, or from about 60 to about 800 seconds, or from about 100 to about 600 seconds, or from about 200 to about 600 seconds, or from about 300 to about 600 seconds.

A further advantage that may be provided by the sterilization detection device of the present disclosure is that the detection relies on a change in the capacitance/current/ oscillation frequency of the sensing device. Accordingly, no calibration may be required for the sensing device.

The biological indicator may be used to release loads or validate sterilization chamber functionality in healthcare settings. In the scientific setting, the biological indicator may be used to validate the functionality of sterilization chambers, release loads of goods, or validate that a process meets required functionality.

While the present disclosure has been explained in relation to various embodiments, it is to be understood that various modifications thereof will become apparent to those skilled in the art upon reading the specification. Therefore, it is to be understood that the disclosure described herein includes any such modifications that may fall within the scope of the appended claims.

The invention claimed is:

1. A process for determining the viability of a biological indicator, the process comprising:
    subjecting the biological indicator to a sterilization process in which the biological indicator is exposed to a sterilization medium, the biological indicator comprising test microorganisms on a carrier;
    subsequent to the sterilization process, exposing the biological indicator to a viability detection medium comprising hydrogen peroxide, the exposing the biological indicator to the detection medium comprising the hydrogen peroxide producing a gaseous reaction product when one or more of the test microorganisms are viable; and
    detecting with a sensing device the presence or absence of the gaseous reaction product produced by the biological indicator combined with the viability detection medium, the sensing device comprising an electro-mechanical sensor, wherein the presence of the gaseous reaction product indicates the presence of viable test microorganisms and the absence of the gaseous reaction product indicates the absence of viable test microorganisms.

2. The process of claim 1, wherein combination of viable test microorganisms of the biological indicator and the viability detection medium produces the gaseous reaction product.

3. The process of claim 1, wherein viable test microorganisms of the biological indicator produce a chemical, and combination of the chemical and the viability detection medium produces the gaseous reaction product.

4. The process of claim 3, wherein the chemical produced by the biological indicator comprises peroxidase.

5. The process of claim 1, wherein the electro-mechanical sensor comprises a quartz crystal microbalance comprising a coating on a surface of the substrate configured to absorb the gaseous reaction product produced by the biological indicator.

6. The process of claim 5, wherein the coating comprises a metal oxide.

7. The process of claim 5, wherein the coating comprises an inorganic material.

8. The process of claim 5, wherein the coating comprises an organic material.

9. The process of claim 5, wherein the coating comprises a polymer.

10. The process of claim 5, wherein the coating further comprises an additive to increase attraction to the gaseous reaction product or catalyze the gas.

11. The process of claim 1, wherein the sensing device comprises an electronic device capable of measuring a change in a frequency of oscillation of the electro-mechanical sensor when the gaseous reaction product interacts with a coating of the electro-mechanical sensor, the change in the frequency indicating the presence of viable test microorganisms.

12. The process of claim 1, wherein the biological indicator comprises bacterial spores.

13. The process of claim 1, wherein the biological indicator comprises bacteria.

14. The process of claim 1, wherein the biological indicator comprises bacteria of the *Bacillus* or *Clostridia* genera.

15. The process of claim 1, wherein the biological indicator comprises *Geobacillus stearothermophilus, Bacillus atrophaeus, Bacillus subtilis, Bacillus pumilus, Bacillus coagulans, Clostridium sporogenes, Bacillus subtilis globigii, Bacillus cereus, Bacillus circulans*, or a mixture of two or more thereof.

16. The process of claim 1, wherein the gaseous reaction product comprises a volatile organic compound.

17. The process of claim 1, wherein the gaseous reaction product comprises carbon dioxide.

18. The process of claim 1, wherein the gaseous reaction product comprises oxygen.

19. The process of claim 1, wherein the gaseous reaction product comprises methane.

20. The process of claim 1, wherein the step of detecting the presence or absence of the gaseous reaction product is conducted under vacuum.

21. The process of claim 1, wherein the sterilization medium comprises steam, dry heat, radiation, plasma, ozone, vaporized hydrogen peroxide, vaporized peracetic acid, chlorine dioxide, one or more gaseous sterilants, and/or one or more liquid sterilants.

22. The process of claim 1, wherein the biological indicator is placed in a sterilization indicator subsequent to being subjected to the sterilization process, the sterilization indicator comprising:
    a container configured to contain the biological indicator;
    a liquid dispenser containing the viability detection medium and arranged to bring the viability detection medium into contact with the biological indicator in the container; and
    the sensing device disposed in the container.

23. The process of claim 22, wherein the container further comprises a vacuum port, and the method further comprises drawing a vacuum in the container prior to exposing the biological indicator to the viability detection medium.

24. The process of claim 1, wherein the biological indicator is contained in a sterilization indicator during the sterilization process, the sterilization indicator comprising a container comprising:
    a first compartment holding the biological indicator;
    a second compartment connected to the first compartment and holding a frangible ampoule containing the viability detection medium;
    a third compartment connected to the first compartment and holding the sensing device disposed in the container; and
    a lid moveable between an open and a closed position, wherein the sterilization process is conducted with the lid in the open position such that at least the first compartment is exposed to external environment.

25. The process of claim 24, wherein the exposing the biological indicator to a viability detection medium comprises closing the lid to break the frangible ampoule and isolate the first compartment, the second compartment, and the third compartment from the external environment.

* * * * *